US011639528B2

(12) United States Patent
Adami et al.

(10) Patent No.: US 11,639,528 B2
(45) Date of Patent: May 2, 2023

(54) PROCESS FOR THE IDENTIFICATION OF PATIENTS AT RISK FOR OSCC

(71) Applicants: Arphion LTD, Chicago, IL (US); THE BOARD OF TRUSTEES OF THE UNIVERSITY OF ILLINOIS, Urbana, IL (US)

(72) Inventors: Guy Adami, Brookfield, IL (US); Yalu Zhou, Chicago, IL (US); Joel Schwartz, Chicago, IL (US); Antonia Kolokythas, Skokie, IL (US)

(73) Assignees: BOARD OF TRUSTEES OF THE UNIVERSITY OF ILLINOIS, Urbana, IL (US); Arphion LTD, Chicago, IL (US)

( * ) Notice: Subject to any disclaimer, the term of this patent is extended or adjusted under 35 U.S.C. 154(b) by 0 days.

(21) Appl. No.: 15/774,005

(22) PCT Filed: Nov. 5, 2016

(86) PCT No.: PCT/US2016/060551
§ 371 (c)(1),
(2) Date: May 5, 2018

(87) PCT Pub. No.: WO2017/079571
PCT Pub. Date: May 11, 2017

(65) Prior Publication Data
US 2018/0327853 A1 Nov. 15, 2018

Related U.S. Application Data

(60) Provisional application No. 62/416,766, filed on Nov. 3, 2016, provisional application No. 62/251,506, filed on Nov. 5, 2015.

(51) Int. Cl.
*C12Q 1/6886* (2018.01)

(52) U.S. Cl.
CPC ..... *C12Q 1/6886* (2013.01); *C12Q 2600/158* (2013.01); *C12Q 2600/178* (2013.01)

(58) Field of Classification Search
CPC ............ C12Q 1/6886; C12Q 2600/158; C12Q 2600/178
See application file for complete search history.

(56) References Cited

U.S. PATENT DOCUMENTS

| | | | | |
|---|---|---|---|---|
| 8,153,370 | B2 | 4/2012 | Adami et al. | |
| 9,920,374 | B2 | 3/2018 | Brody et al. | |
| 2009/0239231 | A1* | 9/2009 | Adami | C12Q 1/6886 435/6.14 |
| 2009/0031782 | A1 | 12/2009 | Wong et al. | |
| 2009/0317820 | A1* | 12/2009 | Wong | C12Q 1/6809 435/6.14 |
| 2010/0017865 | A1 | 7/2010 | Aharonov et al. | |
| 2010/0178653 | A1* | 7/2010 | Aharonov | C12N 15/111 435/6.14 |
| 2011/0007676 | A1 | 3/2011 | Inazawa et al. | |
| 2011/0076768 | A1* | 3/2011 | Inazawa | C12Q 1/6886 435/375 |
| 2013/0018417 | A1 | 7/2013 | Beaudenon-Huibregtse et al. | |
| 2013/0184175 | A1 | 7/2013 | Beaudenon-Huibregtse et al. | |
| 2014/0032235 | A1 | 10/2014 | Goel et al. | |
| 2014/0322354 | A1 | 10/2014 | Goel et al. | |
| 2015/0001822 | A1 | 1/2015 | Taylor et al. | |
| 2015/0018227 | A1 | 1/2015 | Taylor et al. | |

FOREIGN PATENT DOCUMENTS

| | | | |
|---|---|---|---|
| WO | 2010/09337 | A1 | 8/2010 |
| WO | 20150026827 | A1 | 2/2015 |

OTHER PUBLICATIONS

Of Park et al (Clinical Chemistry (2006) 52(6):988-994). (Year: 2006).*
Simon et al. (Cancer Informatics (2007); 3:11-7; cited in the specification) (Year: 2007).*
Wong et al. (Human Cancer Biology (2008) 14(9):2588-2592). (Year: 2008).*
Kolokythas et al. (Journal of Oral Pathology & Medicine (2013); 42(9):663-9; cited in the specification) (Year: 2013).*
Inchley (BMC Infectious Disease (2015) 15(150): 11 pages). (Year: 2015).*

(Continued)

*Primary Examiner* — J. E. Angell
(74) *Attorney, Agent, or Firm* — Lawrence S. Pope

(57) ABSTRACT

The present disclosure involves a process to identify a patient likely to have OSCC by taking a sample containing miRNA from epithelial cells from the patient's oral cavity and determining the relative level of expression of miRNA sequences which have different levels of expression in epithelial cell OSCC tissue than in benign tissue. The epithelial cells are those that form the mucosal epithelium that consists mainly of keratinocytes with some immune cells. It involves determining the relative level of expression of at least miRNA sequences hsa-miR-130-3p, hsa-miR-7-5p, hsa-miR-101-3p and hsa-miR-146b-5p. It also involves discriminating between benign oral lesions and OSCC using a sample of epithelial cells of the lesion and determining the relative level of expression of miRNA sequences which have different levels of expression in epithelial cell OSCC tissue than in benign tissue. It uses the relative level of expression of at least miRNA sequences hsa-miR-196a-5p and hsa-miR-873-5p.

20 Claims, 3 Drawing Sheets

(56) References Cited

OTHER PUBLICATIONS

Mar. 5, 2018 International Preliminary Report on Patentability In WO2017/079571.
Tam et al. article "Robust global microRNA expression profiling using next-generation sequencing technologies" at pp. 350-358 of vol. 94 of Laboratory Investigation (2014).
Alles et al. article "An estimate of the total number of true human miRNAs" at pp. 3353-3364 of vol. 47 of Nucleic Acid Research (2019).
Kolokythas, Antonia et al., "Similar Squamous Cell Carcinoma Epithelium microRNA Expression in Never Smokers and Ever Smokers", PLOS One, Nov. 6, 2015, pp. 1-16, 10(11).
He, Qianting, "microRNA-21 and microRNA-375 from oral cytology as biomarkers for oral tongue cancer detection", Oral Oncol. Jun. 2016 pp. 15-20, 57.

* cited by examiner

PROCESS FOR THE IDENTIFICATION OF PATIENTS AT RISK FOR OSCC

RELATED APPLICATIONS

This application claims priority to U.S. Provisional Application Ser. No. 62/251,506 filed 5 Nov. 2015 and U.S. Provisional Application Ser. No. 62/416,766 filed 3 Nov. 2016, both incorporated herein by reference.

BACKGROUND

The projection for 2012 of oral cancer diagnosis was approximately 30,000 people in the United States, and close to 400,000 in the world. In large regions of Southeast Asia it is the second most-diagnosed cancer. The disease is typically found on the surface of the tongue or gingiva, but can occur anywhere in the oral mucosa. Over 90% of oral cancers are oral squamous cell carcinoma (OSCC). While oral lesions are easily detectable by dentists, only a small percentage will be OSCC. The initial diagnosis requires scalpel biopsy by an oral surgeon, followed by histopathology examination. Because the majority go undiagnosed until the late stages, the disease often has a poor prognosis with average survival times of less than 5 years. Much effort has gone into improving lesion detection and diagnosis and one way is to remove the need for scalpel biopsy. This has been attempted by using special scanning devices based on either infrared light or fluorescence. These approaches have the possibility of easing patient concerns about surgical biopsy while also potentially making it possible to detect and diagnose in one step. Others have used gene-based methods to determine changes in the oral mucosa indicative of cancer. First with mRNA, and then miRNA, RNA signatures for OSCC have been developed using surgically obtained tissue. Results from these surgical specimens, which contain a variable mixture of epithelium and tumor stroma, produce different results between studies. A second approach has looked for markers of OSCC in body fluids, such as blood or saliva, with interesting, but likely due to low RNA concentrations, variable results. The limited follow-up on published RNA classifiers for OSCC combined with the lack of standardized sample collection methods for RNA-based detection and diagnosis has slowed validation for clinical purposes.

The question remains whether improvements in sensitivity and specificity for consistent detection of critical epithelial change will ever allow identification of an RNA signature for OSCC, even under conditions where tissues are dissected and prepared uniformly. The release of The Cancer Genome Atlas (TCGA) dataset of head and neck cancers allows one to address this question as the samples were harvested surgically with uniform methods with reports of levels of normal tissue and stroma in each OSCC sample prior to RNA purification, and there was sufficient number of samples to allow extensive validation. OSCC's have been reported to fall into discrete groups based on mRNA and miRNA expression. Because of that the variety of RNA expression associated with OSCC there was a concern that it may be too complex to allow the creation of a single RNA signature associated with OSCC.

SUMMARY

The present invention involves a process to identify a patient likely to have OSCC comprising taking a sample containing miRNA from epithelial cells from the patient's oral cavity and determining the relative level of expression of miRNA sequences which have different levels of expression in epithelial cell OSCC tissue than in benign tissue. In this regard, the epithelial cells are those that form the mucosal epithelium that consists mainly of keratinocytes with some immune cells as well. In one embodiment it involves determining the relative level of expression of at least the miRNA sequences hsa-miR-130-3p, hsa-miR-7-5p, hsa-miR-101-3p and hsa-miR-146b-5p. In another embodiment it involves it involves a process to discriminate between benign oral lesions and OSCC comprising taking a sample of the epithelial cells of the lesion and determining the relative level of expression of miRNA sequences which have different levels of expression in epithelial cell OSCC tissue than in benign tissue. One embodiment of this discrimination of oral lesions involves determining the relative level of expression of at least the miRNA sequences hsa-miR-196a-5p and hsa-miR-873-5p.

The present invention also involves a process to develop a tool to identify a patient likely to have OSCC comprising taking samples of normal epithelial cells and OSCC epithelial cells, determining the relative level of expression of a selection of miRNA sequences for each of the samples, identifying those miRNA sequences that have statistically different levels of expression in the normal cells compared to the levels of expression in the OSCC cells and applying a statistical tool to create a classifier that to a reasonable degree of accuracy can discriminate between a normal cell and an OSCC cell using the cell's level of expression of selected miRNA sequences. The tool may also be applied to serum or plasma samples. It is expected that the miRNA isolated from these sources will reflect the levels of expression in epithelial cells.

DETAILED DESCRIPTION

Figure 1A:
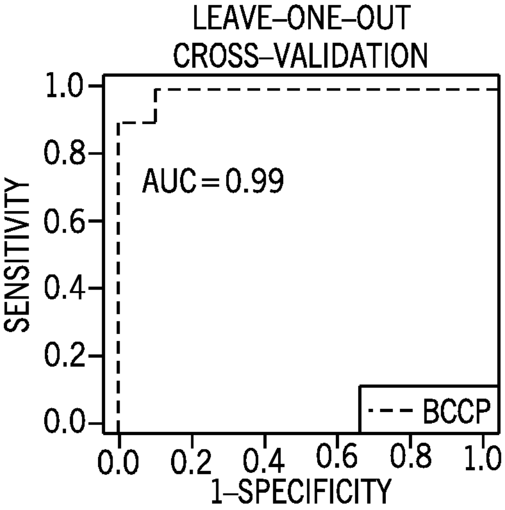
FIG. 1 is a set of six receiver operating characteristic curves (ROC's) for analysis of the TCGA data.
Figure 1B:
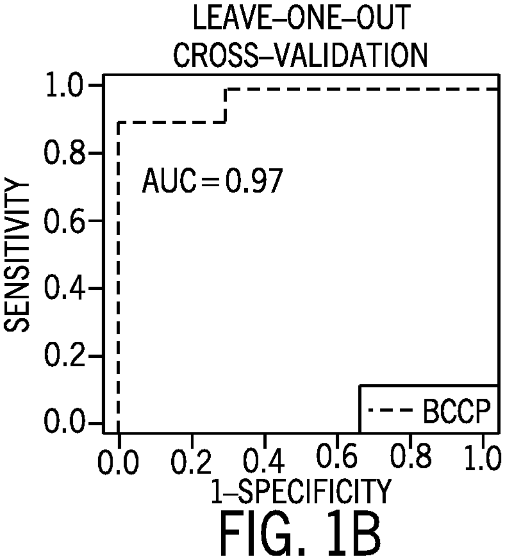
Figure 1C:
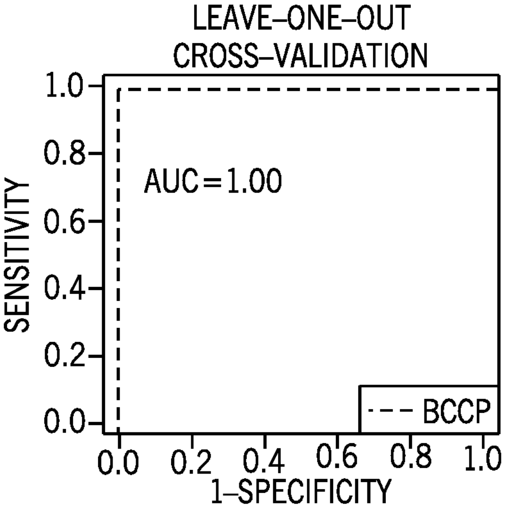
Figure 1D:
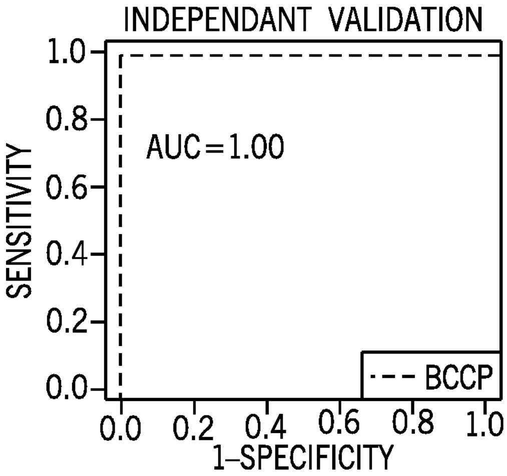
Figure 1E:
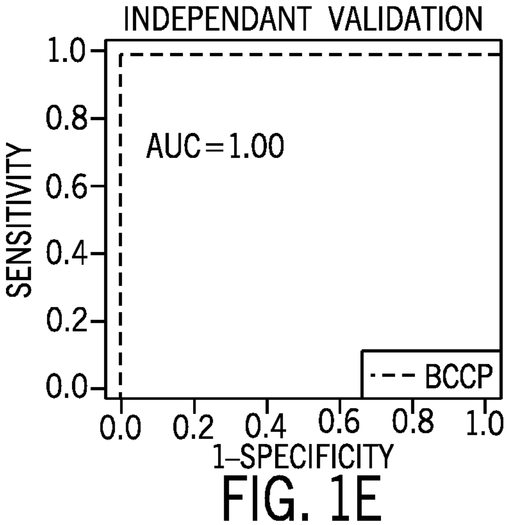
Figure 1F:
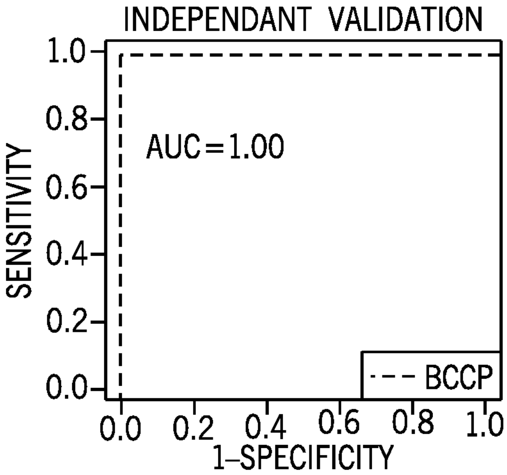

It was determined by data analysis that it was possible to develop a miRNA-based classifier of OSCC using data from surgically obtained specimens collected under the highly standardized conditions of a single large study with uniform sample preparation, i.e. using data from The Cancer Genome Atlas (TCGA) dataset of head and neck cancers. Then data was obtained from samples obtained from brush biopsy of oral mucosa to determine if classifiers could be developed using data from non-invasively obtained samples. The prevalence of various miRNA sequences in samples obtained from epithelial cells of both normal tissue and OSCC tissue was determined by miRNAseq and RT-PCR. The prevalence data was then subjected to statistical analysis to identify those miRNA sequences whose prevalence differed between the epithelial cells of normal tissue and the epithelial cells of OSCC. This analysis identified a number of classifiers that yielded good results. The miRNA sequences in this work and the subsequent brush cytology work were identified in accordance with the miRBase nomenclature available at http://mirbase.org/index.shtml.

Seven algorithms available from the BRB-Array Tools program available from the National Cancer Institute and described in "Analysis of Gene Expression Using BRB-Array Tools by Simon et al. in Cancer Informatics 2007:3, 11-17 were applied to three sets of TCGA data with leave-one-out cross-validation to develop seven classifiers to differentiate tumor from normal control with roughly similar accuracy. In particular, three sets of miRNA prevalence data, each representing ten control samples and ten OSCC samples were used to train classifiers. The so developed classifiers were then validated on an independent set of data drawn from the TCGA dataset representing miRNA prevalence data for ten control samples and 20 OSCC samples.

FIG. 1 displays the results via receiver operating characteristic curves (ROC's) from the original leave-one-out cross-validation and the independent validation for the Bayesian Compound Covariate based classifier. Curves A, B and C show the ROC curves for the original leave-one-out cross-validation of the three sample sets and curves D, E and F show the ROC curves for the independent validation with curves A and D being for the same sample set as are curves B and E and curves C and F.

The miRNA sequences utilized by the three classifiers are set forth in Tables 1-3. In each case the "Fold-change" is prevalence in OSCC in comparison to the prevalence in control using the mean prevalence value of the control set as the base.

TABLE 1

TCGA miRNA Sequences Developed from First Dataset

| | 95% Parametric p-value | Fold-change | UniqueID |
|---|---|---|---|
| 1 | <1e−07 | 0.036 | hsa-mir-204 |
| 2 | <1e−07 | 0.24 | hsa-mir-101-1 |
| 3 | <1e−07 | 6.25 | hsa-mir-550a-1 |
| 4 | 0.0000009 | 0.13 | hsa-mir-29c |
| 5 | 0.0000011 | 0.11 | hsa-let-7c |
| 6 | 0.0000012 | 6.08 | hsa-mir-550a-2 |
| 7 | 0.0000014 | 4.94 | hsa-mir-424 |
| 8 | 0.0000035 | 0.073 | hsa-mir-99a |
| 9 | 0.0000042 | 4.18 | hsa-mir-450b |
| 10 | 0.0000044 | 11 | hsa-mir-503 |
| 11 | 0.0000063 | 7.8 | hsa-mir-455 |
| 12 | 0.0000063 | 2.73 | hsa-mir-324 |
| 13 | 0.0000066 | 0.24 | hsa-mir-139 |
| 14 | 0.0000077 | 21.73 | hsa-mir-31 |
| 15 | 0.0000098 | 4.12 | hsa-mir-16-2 |
| 16 | 0.0000164 | 0.084 | hsa-mir-125b-2 |
| 17 | 0.0000286 | 0.18 | hsa-mir-30a |
| 18 | 0.000029 | 0.47 | hsa-mir-140 |
| 19 | 0.0000308 | 2.71 | hsa-mir-15b |
| 20 | 0.0000337 | 0.34 | hsa-mir-29a |
| 21 | 0.0000419 | 4.9 | hsa-mir-1292 |
| 22 | 0.0000439 | 5.31 | hsa-mir-877 |
| 23 | 0.0000536 | 14.29 | hsa-mir-196b |
| 24 | 0.0000539 | 3.46 | hsa-mir-183 |
| 25 | 0.0000942 | 7.12 | hsa-mir-224 |
| 26 | 0.0000947 | 3.03 | hsa-mir-454 |
| 27 | 0.0001096 | 0.17 | hsa-mir-410 |
| 28 | 0.0001271 | 3.67 | hsa-mir-21 |
| 29 | 0.0001313 | 3.11 | hsa-mir-1301 |
| 30 | 0.0001575 | 6.03 | hsa-mir-1245 |
| 31 | 0.0001767 | 0.19 | hsa-mir-100 |
| 32 | 0.0001779 | 6 | hsa-mir-301a |
| 33 | 0.0001816 | 13.23 | hsa-mir-196a-1 |
| 34 | 0.0001817 | 8.81 | hsa-mir-3648 |
| 35 | 0.0002233 | 3.5 | hsa-mir-193b |
| 36 | 0.0002382 | 2.29 | hsa-mir-576 |
| 37 | 0.0002394 | 0.47 | hsa-mir-30e |
| 38 | 0.0002407 | 2.95 | hsa-mir-484 |
| 39 | 0.0002538 | 3.4 | hsa-mir-3074 |
| 40 | 0.0002541 | 4.1 | hsa-mir-3928 |

TABLE 1-continued

TCGA miRNA Sequences Developed from First Dataset

| | 95% Parametric p-value | Fold-change | UniqueID |
|---|---|---|---|
| 41 | 0.0002654 | 0.037 | hsa-mir-375 |
| 42 | 0.000281 | 0.25 | hsa-mir-195 |
| 43 | 0.0002919 | 3.8 | hsa-mir-450a-2 |
| 44 | 0.0003267 | 0.29 | hsa-mir-125b-1 |
| 45 | 0.0004122 | 2.26 | hsa-mir-1306 |
| 46 | 0.000435 | 3.28 | hsa-mir-450a-1 |
| 47 | 0.0004397 | 2.63 | hsa-mir-96 |
| 48 | 0.0004456 | 11.05 | hsa-mir-937 |
| 49 | 0.000449 | 7.71 | hsa-mir-615 |
| 50 | 0.0004689 | 4.12 | hsa-mir-2355 |

TABLE 2

TCGA miRNA Sequences Developed from Second Dataset

| | 90% Parametric p-value | Fold-change | UniqueID |
|---|---|---|---|
| 1 | <1e−07 | 0.22 | hsa-mir-101-1 |
| 2 | 0.0000013 | 0.098 | hsa-mir-125b-2 |
| 3 | 0.0000018 | 0.091 | hsa-mir-99a |
| 4 | 0.0000028 | 7.15 | hsa-mir-4326 |
| 5 | 0.0000033 | 0.11 | hsa-let-7c |
| 6 | 0.0000185 | 2.68 | hsa-mir-130b |
| 7 | 0.0000201 | 2.07 | hsa-mir-423 |
| 8 | 0.0000358 | 36.4 | hsa-mir-196a-1 |
| 9 | 0.0000433 | 0.51 | hsa-mir-30e |
| 10 | 0.0000604 | 2.38 | hsa-mir-671 |
| 11 | 0.0001043 | 3.84 | hsa-mir-1301 |
| 12 | 0.0001127 | 10.78 | hsa-mir-196b |
| 13 | 0.0001289 | 2.08 | hsa-mir-501 |
| 14 | 0.0002065 | 4.63 | hsa-mir-3662 |
| 15 | 0.000234 | 9.48 | hsa-mir-1293 |
| 16 | 0.0003316 | 2.25 | hsa-mir-197 |
| 17 | 0.0004565 | 0.33 | hsa-mir-100 |

TABLE 3

TCGA miRNA Sequences Developed from Third Dataset

| | 100% Parametric p-value | Fold-change | UniqueID |
|---|---|---|---|
| 1 | 0.000001 | 0.22 | hsa-mir-101-2 |
| 2 | 0.0000032 | 0.26 | hsa-mir-101-1 |
| 3 | 0.0000074 | 0.081 | hsa-mir-204 |
| 4 | 0.0000137 | 0.11 | hsa-mir-891a |
| 5 | 0.0000084 | 0.4 | hsa-mir-140 |
| 6 | 0.0000138 | 0.19 | hsa-mir-99a |
| 7 | 0.0000216 | 0.25 | hsa-mir-1468 |
| 8 | 0.0000388 | 0.17 | hsa-mir-410 |
| 9 | 0.0000446 | 0.18 | hsa-mir-30a |
| 10 | 0.0000482 | 0.26 | hsa-mir-432 |
| 11 | 0.0000491 | 0.23 | hsa-mir-29c |
| 12 | 0.0000645 | 0.036 | hsa-mir-375 |
| 13 | 0.0001122 | 0.35 | hsa-mir-195 |
| 14 | 0.0001866 | 0.29 | hsa-mir-487b |
| 15 | 0.0002036 | 0.35 | hsa-mir-100 |
| 16 | 0.000212 | 0.23 | hsa-mir-125b-2 |
| 17 | 0.0002185 | 0.23 | hsa-mir-376c |
| 18 | 0.0003111 | 0.35 | hsa-mir-656 |
| 19 | 0.0002901 | 0.45 | hsa-mir-125b-1 |
| 20 | 0.0003015 | 0.25 | hsa-let-7c |
| 21 | 0.0003401 | 0.13 | hsa-mir-381 |
| 22 | 0.0003673 | 0.37 | hsa-mir-889 |
| 23 | 0.0003979 | 0.28 | hsa-mir-431 |
| 24 | 0.0004061 | 0.29 | hsa-mir-369 |
| 25 | 0.0004301 | 0.19 | hsa-mir-299 |
| 26 | 0.0004378 | 0.44 | hsa-mir-30e |
| 27 | 0.0004526 | 0.26 | hsa-mir-217 |

TABLE 3-continued

TCGA miRNA Sequences Developed from Third Dataset

| | 100% Parametric p-value | Fold-change | UniqueID |
|---|---|---|---|
| 28 | 0.0004923 | 2.52 | hsa-mir-421 |
| 29 | 0.0004873 | 4.17 | hsa-mir-3677 |
| 30 | 0.0004682 | 2.54 | hsa-mir-584 |
| 31 | 0.0004323 | 2.89 | hsa-mir-550a-2 |
| 32 | 0.0004002 | 5.17 | hsa-mir-944 |
| 33 | 0.0003761 | 2.43 | hsa-mir-181b-1 |
| 34 | 0.0003667 | 3.34 | hsa-mir-183 |
| 35 | 0.000346 | 2.21 | hsa-mir-15b |
| 36 | 0.0003771 | 3.33 | hsa-mir-940 |
| 37 | 0.0003717 | 2.9 | hsa-mir-939 |
| 38 | 0.0003159 | 2.49 | hsa-mir-505 |
| 39 | 0.0002991 | 1.69 | hsa-mir-652 |
| 40 | 0.0003796 | 4.79 | hsa-mir-3928 |
| 41 | 0.0002877 | 3.79 | hsa-mir-592 |
| 42 | 0.0002729 | 3.41 | hsa-mir-550a-1 |
| 43 | 0.000253 | 2.79 | hsa-mir-92b |
| 44 | 0.0002139 | 2.33 | hsa-mir-330 |
| 45 | 0.0002045 | 3.19 | hsa-mir-222 |
| 46 | 0.0001767 | 1.92 | hsa-mir-148b |
| 47 | 0.0002633 | 3.27 | hsa-mir-3922 |
| 48 | 0.0001621 | 3.9 | hsa-mir-21 |
| 49 | 0.0001471 | 1.87 | hsa-mir-106b |
| 50 | 0.0001243 | 2.93 | hsa-mir-1301 |
| 51 | 0.000116 | 3.74 | hsa-mir-3934 |
| 52 | 0.0000935 | 4.31 | hsa-mir-450a-2 |
| 53 | 0.0000703 | 2.08 | hsa-let-7d |
| 54 | 0.0000681 | 6.3 | hsa-mir-301a |
| 55 | 0.0000785 | 2.58 | hsa-mir-3074 |
| 56 | 0.0000508 | 3.22 | hsa-mir-1307 |
| 57 | 0.000041 | 2.68 | hsa-mir-450b |
| 58 | 0.000025 | 4 | hsa-mir-3605 |
| 59 | 0.0000112 | 4.12 | hsa-mir-2355 |
| 60 | 0.000011 | 2.91 | hsa-mir-766 |
| 61 | 0.0000098 | 2.72 | hsa-mir-744 |
| 62 | 0.0000087 | 3.17 | hsa-mir-331 |
| 63 | 0.000006 | 3.61 | hsa-mir-345 |
| 64 | 0.0000052 | 2.38 | hsa-mir-7-1 |
| 65 | 0.0000039 | 3.29 | hsa-mir-130b |
| 66 | 0.0000035 | 11.34 | hsa-mir-877 |
| 67 | 0.0000019 | 2.63 | hsa-mir-671 |
| 68 | 0.0000016 | 38.08 | hsa-mir-196a-1 |
| 69 | 0.0000008 | 12.77 | hsa-mir-503 |
| 70 | 0.000001 | 9.27 | hsa-mir-937 |
| 71 | 0.0000063 | 7.94 | hsa-mir-1910 |
| 72 | 0.0000005 | 4.66 | hsa-mir-193b |
| 73 | 0.0000004 | 3.86 | hsa-mir-324 |
| 74 | 0.0000004 | 40.46 | hsa-mir-196b |
| 75 | 0.0000232 | 24.39 | hsa-mir-615 |
| 76 | 0.0000002 | 7.7 | hsa-mir-187 |
| 77 | 0.0000002 | 2.87 | hsa-mir-1306 |
| 78 | 0.0000002 | 6.21 | hsa-mir-424 |
| 79 | 0.0000002 | 13.81 | hsa-mir-3940 |
| 80 | $<1e-07$ | 10.39 | hsa-mir-455 |

Experiments were then done to obtain data from non-invasive oral samples. In particular, samples were taken by brush cytology and processed to yield miRNA prevalence data as detailed in the working examples. Initially the samples were interrogated with miRNAseq, but not all the samples contained sufficient miRNA to yield meaningful results. Subsequently the samples were interrogated with qRT-PCR. While this latter technique requires a pre-selection of the miRNA sequences to be examined, it is more sensitive and thus yields results when a lower concentration of miRNA is present.

Figure 2:
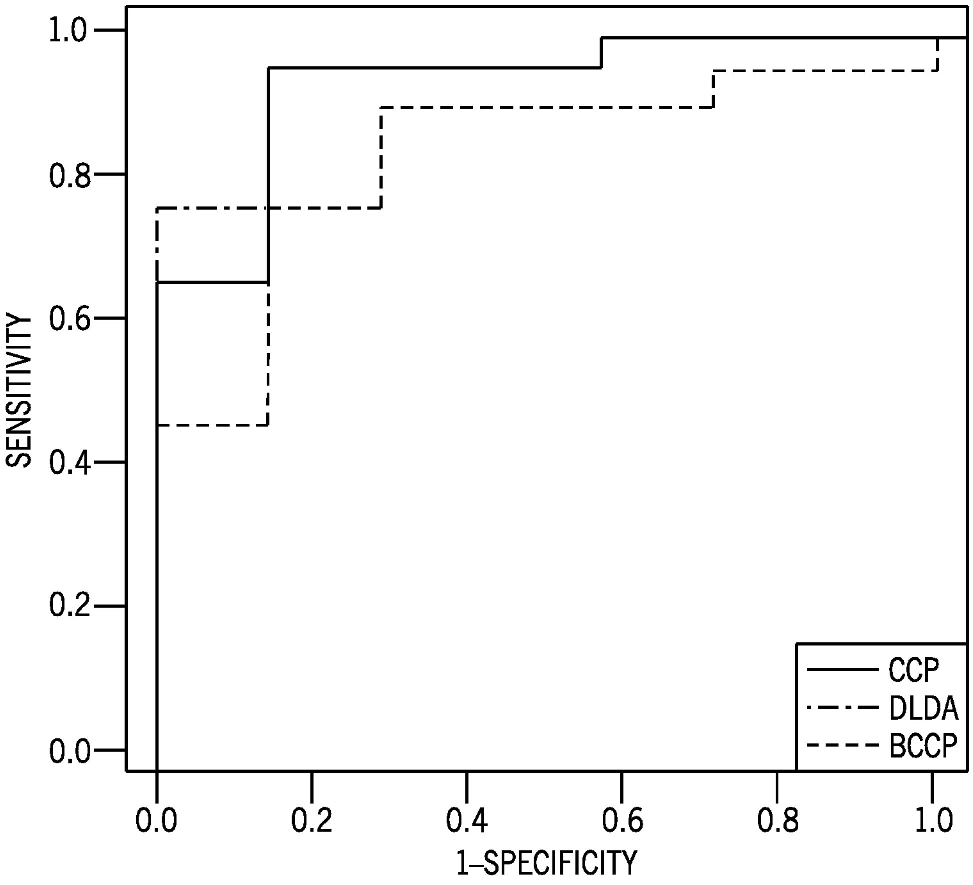
FIG. 2 is a set of 3 receiver operating characteristic curves (ROC's) for analysis of the oral brush cytology data obtained by use of miRNA seq.

The application of the BRB-Array Tools to the miRNAseq data obtained from 20 samples from OSCC tissue and 7 control samples using a False Discover Rate (FDR) of 0.10 identified the 13 of the 15 miRNA sequences listed in Table 4. Seven different statistical tools from the BRB-Array Tools suite were applied to the sequence data and algorithms were developed, which utilized the fifteen sequence listed in Table 4. These algorithms were tested using leave-one-out cross-validation, which revealed 87% accuracy on average in differentiating tumor versus normal control. Receiver operating characteristic curves for three representative types of OSCC classifiers obtained by this application of BRB-Array Tools are shown in FIG. 2. A ROC curve is shown for each of Compound Covariate (CCP), Diagonal Linear Discriminant Analysis (DLDA) and Bayesian Compound Covariate Predictor (BCCP).

TABLE 4 miRNA Sequences from miRNAseq Data

| | Parametric p-value | Fold-change | Unique ID |
|---|---|---|---|
| 1 | 0.0002033 | 4 | hsa-miR-3605-3p |
| 2 | 0.0002462 | 11.22 | hsa-miR-10a-5p |
| 3 | 0.000332 | 13.07 | hsa-miR-10b-5p |
| 4 | 0.0003518 | 5.08 | hsa-miR-185-3p |
| 5 | 0.0011606 | 4.38 | hsa-miR-424-5p |
| 6 | 0.0013125 | 4.8 | hsa-miR-99b-3p |
| 7 | 0.0016351 | 1.89 | hsa-miR-339-5p |
| 8 | 0.0022419 | 2.42 | hsa-miR-328-3p |
| 9 | 0.0029416 | 5.33 | hsa-miR-126-5p |
| 10 | 0.0034308 | 2.71 | hsa-miR-31-3p |
| 11 | 0.004026 | 0.57 | hsa-miR-200b-5p |
| 12 | 0.0041133 | 21.09 | hsa-miR-196a-5p |
| 13 | 0.0059159 | 9.12 | hsa-miR-190a-5p |
| 14 | 0.0079018 | 2.11 | hsa-miR-31-5p |
| 15 | 0.0086229 | 3.44 | hsa-miR-766-3p |

Figure 3:
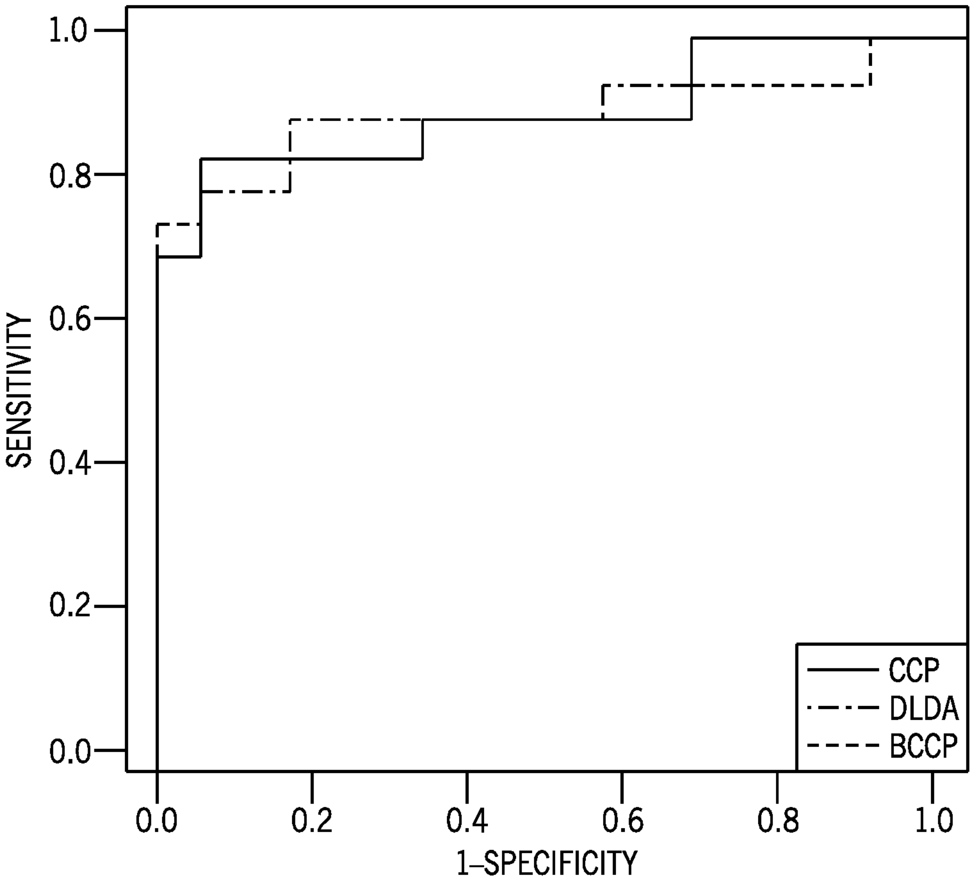
FIG. 3 is a set of 3 receiver operating characteristic curves (ROC's) for analysis of the oral brush cytology data obtained by use of qRT-PCR.

The interrogation with qRT-PCR was able to extract useful data from 20 OSCC samples and 17 control samples to yield a list of 46 miRNA sequence that showed differential expression at a False Discovery Rate (FDR) of 0.10. Forty-three of these sequences, listed in Table 5, were utilized by six of the statistical tools in the BRB-Array Tools suite using leave-one-out cross-validation to create 6 different types of OSCC RNA-based classifiers that on average distinguished tumor from normal with 87% accuracy. A ROC curve is shown in FIG. 3 for each of Compound Covariate (CCP), Diagonal Linear Discriminant Analysis (DLDA) and Bayesian Compound Covariate Predictor (BCCP).

TABLE 5 miRNA Sequences from qRT-PCR Data

| | Parametric p-value | Fold-change | UniqueID |
|---|---|---|---|
| 1 | 0.0000096 | 47.03 | hsa-miR-486-5p |
| 2 | 0.0000407 | 6 | hsa-mir-7-5p |
| 3 | 0.0000535 | 2.59 | hsa-miR-146b-5p |
| 4 | 0.0000667 | 0.51 | hsa-miR-130b-3p |
| 5 | 0.0000683 | 2.65 | hsa-miR-101-3p |
| 6 | 0.0000869 | 2.02 | hsa-miR-18b-5p |
| 7 | 0.0001101 | 43.97 | hsa-miR-10b-5p |
| 8 | 0.0001448 | 2.65 | hsa-miR-21-5p |
| 9 | 0.0001769 | 8.23 | hsa-miR-190a |
| 10 | 0.000233 | 5.55 | hsa-miR-20b-5p |
| 11 | 0.0002736 | 7.39 | hsa-miR-126-3p |
| 12 | 0.0002888 | 4.66 | hsa-miR-31-5p |
| 13 | 0.0003458 | 0.48 | hsa-miR-34a-5p |
| 14 | 0.0004278 | 3.5 | hsa-miR-100-5p |
| 15 | 0.0004544 | 1.95 | hsa-miR-19a-3p |
| 16 | 0.0005441 | 8.3 | hsa-miR-199a-5p |
| 17 | 0.000667 | 0.32 | hsa-miR-296-5p |
| 18 | 0.0006819 | 1.84 | hsa-miR-18a-5p |
| 19 | 0.0006857 | 0.18 | hsa-miR-885-5p |
| 20 | 0.0007666 | 0.61 | hsa-miR-378a-3p |
| 21 | 0.0008715 | 0.49 | hsa-miR-210 |
| 22 | 0.0009588 | 0.59 | hsa-miR-324-3p |
| 23 | 0.0009687 | 0.16 | hsa-miR-30b-3p |

TABLE 5-continued

| miRNA Sequences from qRT-PCR Data | | | |
|---|---|---|---|
| | Parametric p-value | Fold-change | UniqueID |
| 24 | 0.001268 | 6.85 | hsa-miR-127-3p |
| 25 | 0.0012812 | 0.61 | hsa-miR-365a-3p |
| 26 | 0.0012911 | 1.98 | hsa-miR-194-5p |
| 27 | 0.0014138 | 3.11 | hsa-miR-671-5p |
| 28 | 0.0016244 | 0.042 | hsa-miR-340-5p |
| 29 | 0.0016916 | 0.51 | hsa-miR-423-5p |
| 30 | 0.0017902 | 0.3 | hsa-miR-375 |
| 31 | 0.0017916 | 3.46 | hsa-miR-155-5p |
| 32 | 0.0020139 | 7.19 | hsa-miR-187-3p |
| 33 | 0.0021023 | 1.52 | hsa-miR-17-5p |
| 34 | 0.0022965 | 2.46 | hsa-miR-454-3p |
| 35 | 0.0025843 | 2.96 | hsa-miR-363-3p |
| 36 | 0.0030432 | 1.48 | hsa-miR-106a-5p |
| 37 | 0.0033991 | 0.35 | hsa-miR-218-5p |
| 38 | 0.0034229 | 2.44 | hsa-miR-135b-5p |
| 39 | 0.0044533 | 1.61 | hsa-miR-19b-3p |
| 40 | 0.0044576 | 2.64 | hsa-miR-135a-5p |
| 41 | 0.0045035 | 3.25 | hsa-miR-146a-5p |

TABLE 5-continued

| miRNA Sequences from qRT-PCR Data | | | |
|---|---|---|---|
| | Parametric p-value | Fold-change | UniqueID |
| 42 | 0.0047201 | 0.17 | hsa-miR-345-5p |
| 43 | 0.0047608 | 0.59 | hsa-miR-574-3p |

The data obtained by the application of miRNA seq and qRT-PCR to various patient samples is displayed is Tables 6 and 7, respectively. In Table 6 the normalized log-transformed median-centered prevalence for 10 miRNA sequences is reported for OSCC samples (Class1) and normal samples (Class2). In Tables 7 A through F similar data is reported for 51 miRNA sequences. In this regard, while there is significant overlap in the samples tested, some samples were only interrogated by one of the two sequencing techniques. Various statistical tools were applied to this data to generate classifiers for separating OSCC samples from benign samples. Different statistical tools with different selection criteria use different sets of miRNA sequences to effect the separation as discussed below.

TABLE 6 miRNA Prevalence by miRNAseq

| Sample ID | Class | 1 hsa-miR-10a-5p | 2 hsa-miR-10b-5p | 3 hsa-miR-126-5p | 4 hsa-miR-185-3p | 5 hsa-miR-196a-5p | 6 hsa-miR-200b-5p | 7 hsa-miR-31-3p | 8 hsa-miR-328-3p | 9 hsa-miR-3605-3p | 10 hsa-miR-424-5p | 11 hsa-miR-99b-3p |
|---|---|---|---|---|---|---|---|---|---|---|---|---|
| 231 | 1 | 8.889 | 11.936 | 10.848 | 6.982 | | 11.23 | 10.304 | 8.921 | 5.397 | 9.755 | 6.204 |
| 305 | 1 | | 5.952 | 6.827 | 6.952 | | 11.639 | 10.653 | 7.827 | | 9.476 | 4.952 |
| 3553 | 1 | 8.34 | 7.34 | | 8.34 | | | 8.34 | 9.662 | 7.34 | 12.469 | |
| 357 | 1 | 8.863 | 11.448 | 7.404 | 6.726 | 12.623 | 11.404 | 11.393 | 8.311 | | 10.404 | |
| 413 | 1 | 5.563 | 8.563 | | 7.563 | 8.37 | 11.446 | 9.811 | 9.955 | 5.563 | 9.885 | 6.563 |
| 453 | 1 | 11.794 | 12.481 | 10.189 | 7.751 | 10.396 | 10.343 | 11.1 | 9.739 | 5.966 | 10.617 | 7.654 |
| 463 | 1 | 9.05 | 11.422 | | 6.962 | 10.744 | 10.869 | 11.757 | 8.663 | 6.547 | 10.05 | 6.547 |
| 4231 | 1 | 7.591 | 10.886 | 9.686 | 6.453 | 5.131 | 11.498 | 8.591 | 8.301 | | 10.716 | 6.453 |
| 4281 | 1 | | 10.974 | | 7.515 | 9.837 | 10.974 | 10.422 | 9.974 | 6.515 | 8.837 | |
| 4291 | 1 | | 6.774 | | 6.774 | 6.038 | 11.54 | 9.976 | 8.622 | 6.038 | 11.139 | |
| 5271 | 1 | 8.398 | 7.472 | 11.033 | 6.472 | | 11.238 | 8.958 | 8.543 | | 10.932 | |
| 129129 | 1 | | | 7.381 | 9.966 | | 10.189 | 9.703 | 11.629 | | | |
| 359 | 1 | 7.82 | 7.82 | | 9.405 | | 10.405 | 11.28 | 9.82 | | 7.82 | |
| 383 | 1 | 10.004 | 11.721 | 9.035 | 9.156 | 10.852 | 10.662 | 11.24 | 8.904 | 5.512 | 9.904 | 7.682 |
| 449 | 1 | 6.065 | 10.065 | 9.065 | 9.235 | 8.65 | 9.065 | 8.65 | 9.765 | | 11.152 | 7.065 |
| 485 | 1 | 8.819 | 9.404 | 9.334 | 9.404 | 10.297 | 10.471 | 9.712 | 9.471 | 6.012 | 9.767 | 7.597 |
| 466 | 1 | 8.009 | 9.331 | 6.009 | | 9.179 | 10.257 | 8.816 | 9.331 | | 9.179 | 7.594 |
| 583 | 1 | 8.73 | 13.087 | 7.73 | | 9.73 | 10.9 | 10.537 | | | 10.315 | 7.73 |
| 587 | 1 | | 7.64 | 10.962 | | 9.225 | 9.64 | | 10.225 | | 11.727 | 8.64 |
| 589 | 1 | 7.199 | 9.199 | 7.199 | | 7.199 | 11.007 | 9.521 | 8.2 | 7.199 | 11.954 | 8.784 |
| 1920.1 | 2 | 3.576 | 5.161 | 5.898 | 4.576 | | 11.631 | 7.824 | 7.161 | 3.576 | 8.035 | 5.576 |
| 28.2 | 2 | 7.039 | 9.38 | 7.832 | 5.939 | 3.132 | 11.721 | 9.014 | 8.686 | 5.132 | 10.747 | 4.717 |
| 514 | 2 | 4.995 | 5.995 | 5.995 | | 4.995 | 11.534 | 7.317 | 7.995 | 4.995 | 9.455 | |
| 518517 | 2 | 3.511 | 5.096 | 6.318 | 4.511 | | 11.211 | 9.393 | 8.034 | 3.511 | 8.511 | 3.511 |
| 540 | 2 | | 6.238 | 6.238 | 6.238 | | 11.56 | 9.045 | 8.56 | | 6.238 | |
| 543 | 2 | 5.15 | 5.15 | 7.15 | 5.15 | 6.15 | 11.559 | 9.472 | 7.472 | | 7.957 | |
| 548 | 2 | | 5.418 | 3.833 | 6.64 | | 12.085 | 8.155 | 8.003 | 3.833 | 5.833 | 5.418 |

TABLE 7A miRNA prevalence by qRT-PCR

| Sample ID | Class | 1 hsa-mir-7-5p | 2 hsa-miR-218 | 3 hsa-miR-31-3p | 4 hsa-miR-210 | 5 hsa-miR-194-5p | 6 hsa-miR-486-5p | 7 hsa-miR-378a-3p | 8 hsa-miR-423-5p | 9 hsa-miR-574-3p |
|---|---|---|---|---|---|---|---|---|---|---|
| 231 | 1 | −2.449 | −2.968 | −2.57 | 4.371 | −2.185 | −0.351 | 2.19 | 0.789 | −0.21 |
| 305K | 1 | −6.232 | −2.073 | −3.707 | 5.84 | −2.752 | | 3.118 | 2.806 | −0.124 |
| 308 | 1 | | −3.048 | −1.094 | 4.982 | −3.269 | −7.426 | 2.623 | 1.866 | 0.447 |

TABLE 7A-continued miRNA prevalence by qRT-PCR

| Sample ID | Class | 1 hsa-mir-7-5p | 2 hsa-miR-218 | 3 hsa-miR-31-3p | 4 hsa-miR-210 | 5 hsa-miR-194-5p | 6 hsa-miR-486-5p | 7 hsa-miR-378a-3p | 8 hsa-miR-423-5p | 9 hsa-miR-574-3p |
|---|---|---|---|---|---|---|---|---|---|---|
| 355 | 1 | −2.196 | −6.291 | −7.794 | 3.075 | −1.071 | | 2.043 | 1.152 | −2.335 |
| 357 | 1 | −2.857 | −5.067 | −1.682 | 3.819 | −2.364 | −0.884 | 1.888 | 0.659 | −1.568 |
| 413 | 1 | −5.035 | −3.356 | −2.46 | 4.053 | −4.445 | −6.425 | 2.587 | 1.835 | 0.315 |
| 453 | 1 | −1.814 | −6.918 | −1.063 | 3.346 | −2.287 | 1.087 | 2.467 | 1.593 | −0.867 |
| 463 | 1 | −3.186 | −8.177 | 0.479 | 5.545 | −1.02 | −3.518 | 3.295 | 2.287 | −1.544 |
| 42810 | 1 | | −6.081 | −1.253 | 5.739 | −2.909 | −5.03 | 2.886 | 2.322 | 0.199 |
| 42310 | 1 | −4.473 | −4.143 | −1.931 | 4.402 | −2.372 | −0.155 | 1.817 | 1.252 | −0.45 |
| 42910 | 1 | −3.857 | −3.032 | 0.481 | 3.766 | −2.183 | −7.079 | 2.674 | 0.288 | −0.219 |
| 52710 | 1 | −2.872 | −5.558 | −1.017 | 4.09 | −1.069 | 2.166 | 1.579 | 0.947 | −0.495 |
| 110 | 1 | −4.154 | −6.059 | 0.986 | 4.005 | −2.115 | −0.488 | 2.178 | 1.139 | −1.029 |
| 129 | 1 | −1.754 | −6.168 | 0.455 | 3.367 | −1.004 | 1.6 | 1.543 | 0.691 | −1.808 |
| 329SCC | 1 | 0.798 | −2.884 | −1.916 | 3.586 | −1.8 | −2.718 | 2.712 | −0.508 | 0.683 |
| 359 | 1 | −2.866 | −2.349 | 0.924 | 3.79 | −1.809 | −1.122 | 2.392 | −0.212 | 0.197 |
| 383 | 1 | −1.658 | −5.864 | 0.312 | 3.419 | −1.009 | 1.575 | 1.648 | 0.881 | −1.672 |
| 449 | 1 | −1.994 | −5.246 | −0.807 | 2.919 | −1.474 | 0.232 | 1.965 | 0.791 | −1.392 |
| 466 | 1 | −2.275 | −5.797 | −1.127 | 3.806 | −2.089 | −3.022 | 2.623 | 0.055 | 0.035 |
| 485 | 1 | −2.039 | −4.862 | −1.209 | 3.974 | −0.519 | 1.526 | 1.832 | −0.072 | −0.455 |
| 1019.2 | 2 | −5.134 | −4.064 | −1.819 | 6.825 | −4.953 | −6.873 | 4.433 | 3.978 | 0.302 |
| 1098 | 2 | −3.179 | −4.191 | −6.354 | 3.511 | −2.378 | | 2.082 | 1.847 | −1.132 |
| 28.2 | 2 | −3.955 | −3.575 | −8.48 | 5.216 | −2.71 | −6.574 | 2.42 | 0.934 | 0.114 |
| 1920.1 | 2 | −3.258 | | −3.026 | 5.889 | −3.139 | −10.868 | 3.736 | 1.526 | 0.909 |
| 426 | 2 | −8.565 | −5.168 | 0.309 | 6.49 | −3.784 | −5.353 | 3.57 | 2.366 | 0.442 |
| 514 | 2 | −5.677 | −2.743 | −2.895 | 5.196 | −2.735 | −7.374 | 2.796 | 1.778 | 0.481 |
| 515 | 2 | −6.612 | −2.855 | −3.325 | 5.276 | −2.335 | −4.282 | 3.27 | 2.122 | 0.321 |
| 518517 | 2 | −3.002 | −2.85 | −4.043 | 4.559 | −2.299 | −5.749 | 2.726 | 1.374 | −0.019 |
| 548 | 2 | −4.728 | −3.599 | −5.252 | 5.382 | −2.185 | −3.561 | 3.497 | 1.669 | 0.362 |
| 109.1 | 2 | −6.451 | −4.225 | −1.013 | 5.296 | −2.704 | −1.75 | 3.334 | 3.188 | −0.209 |
| 104.1 | 2 | −5.093 | −4.276 | −1.933 | 5.262 | −2.912 | −9.75 | 3.49 | 3.011 | 1.226 |
| 115.1 | 2 | −4.839 | −2.618 | −1.43 | 4.509 | −2.986 | −10.372 | 2.592 | 1.52 | −0.347 |
| 117.1 | 2 | −4.328 | −3.225 | −2.605 | 3.782 | −1.855 | −5.992 | 1.861 | 1.465 | −0.366 |
| 111.1 | 2 | −5.787 | −3.551 | −2.511 | 4.874 | −2.991 | −11.29 | 2.635 | 1.84 | 0.657 |
| 100.1 | 2 | −7.713 | −1.283 | −3.119 | 5.823 | −3.421 | −9.47 | 3.538 | 2.406 | 0.632 |
| 114.1 | 2 | −8.154 | −2.33 | −4.957 | 4.751 | −3.771 | −9.098 | 3.272 | 2.197 | −0.202 |
| 101.1 | 2 | −5.562 | −1.852 | −2.751 | 4.335 | −3.385 | | 2.217 | 0.704 | −0.821 |

TABLE 7B miRNA prevalence by qRT-PCR

| Sample ID | Class | 10 hsa-miR-130b-3p | 11 hsa-miR-101-3p | 12 hsa-miR-18a-5p | 13 hsa-miR-423-3p | 14 hsa-miR-126-3p | 15 hsa-miR-301a-3p | 16 hsa-miR-30b-3p | 17 hsa-miR-363-3p | 18 hsa-miR-885-5p |
|---|---|---|---|---|---|---|---|---|---|---|
| 231 | 1 | −3.082 | −0.511 | −0.037 | 0.838 | 1.199 | −1.858 | | −1.685 | −4.041 |
| 305K | 1 | −2.341 | 0.499 | −0.757 | 1.409 | −4.72 | −2.647 | | −4.041 | −3.8 |
| 308 | 1 | −1.998 | −0.159 | −1.038 | 0.603 | −3.545 | −2.401 | −11.839 | −3.258 | −4.375 |
| 355 | 1 | −2.785 | 1.349 | −0.904 | 0.943 | −4.338 | −0.241 | | −4.648 | |
| 357 | 1 | −4.013 | 0.565 | −0.508 | 0.177 | −0.988 | −2.336 | | −2.398 | −10.085 |
| 413 | 1 | −3.445 | 0.043 | −1.226 | 0.905 | −7.645 | −2.295 | −10.566 | −6.284 | −4.641 |
| 453 | 1 | −1.917 | −0.706 | 0.242 | 1.095 | 1.243 | −1.601 | | −1.466 | −9.508 |
| 463 | 1 | −2.17 | −1.086 | 0.447 | 0.57 | −1.901 | −2.145 | | −5.698 | |
| 42810 | 1 | −2.195 | −0.943 | | 2.164 | −4.524 | −1.943 | | −5.393 | −6.344 |
| 42310 | 1 | −3.868 | −0.684 | −1.827 | 1.136 | −0.082 | −2.508 | | −2.946 | |
| 42910 | 1 | −4.042 | 0.881 | −0.577 | 0.386 | −1.925 | −1.553 | −13.182 | −4.55 | −6.301 |
| 52710 | 1 | −3.18 | 1.502 | −0.024 | 0.531 | 1.705 | −0.495 | | −0.418 | −7.261 |
| 110 | 1 | −2.695 | 0.548 | −0.137 | 0.755 | 0.905 | −1.661 | | −1.673 | −5.012 |
| 129 | 1 | −2.999 | −0.368 | 0.144 | −0.575 | 1.741 | −1.618 | −13.543 | −0.571 | −10.681 |
| 329SCC | 1 | −3.353 | 0.19 | 0.188 | 0.693 | −1.528 | −1.206 | | −3.695 | −6.277 |
| 359 | 1 | −3.722 | 0.605 | 0.025 | 0.107 | 1.083 | −1.621 | | −3.365 | −6.587 |
| 383 | 1 | −3.052 | −0.209 | 0.447 | −0.754 | 1.616 | −1.69 | −12.492 | −0.585 | −9.497 |
| 449 | 1 | −2.559 | 0.137 | 0.024 | −0.638 | 0.718 | −1.178 | −12.76 | −1.563 | −12.008 |
| 466 | 1 | −2.269 | −0.209 | 0.646 | 0.489 | −0.298 | 0.044 | −13.844 | −3.5 | −7.173 |
| 485 | 1 | −3.391 | 2.059 | 0.408 | −0.598 | 1.695 | −0.996 | −13.289 | 0.283 | −7.244 |
| 1019.2 | 2 | −0.483 | −2.493 | −1.517 | 2.076 | −5.321 | −2.455 | | −3.911 | −4.507 |
| 1098 | 2 | −2.543 | 1.839 | −1.343 | −0.406 | −4.39 | −0.43 | | −5.051 | −5.115 |
| 28.2 | 2 | −2.369 | −1.049 | −0.581 | 1.454 | −3.023 | −1.574 | −12.706 | −4.631 | −5.436 |
| 1920.1 | 2 | −1.935 | −1.605 | −0.459 | 1.405 | −3.991 | −1.417 | | −3.567 | −4.19 |
| 426 | 2 | −2.231 | −2.382 | −0.732 | 1.753 | −5.505 | −2.577 | | −5.379 | −6.834 |
| 514 | 2 | −1.858 | −1.281 | −1.524 | 0.295 | −4.095 | −2.249 | | −3.754 | −4.104 |

TABLE 7B-continued

| Sample ID | Class | 10 hsa-miR-130b-3p | 11 hsa-miR-101-3p | 12 hsa-miR-18a-5p | 13 hsa-miR-423-3p | 14 hsa-miR-126-3p | 15 hsa-miR-301a-3p | 16 hsa-miR-30b-3p | 17 hsa-miR-363-3p | 18 hsa-miR-885-5p |
|---|---|---|---|---|---|---|---|---|---|---|
| | | miRNA prevalence by qRT-PCR | | | | | | | | |
| 515 | 2 | −1.813 | −1.514 | −0.575 | 1.119 | −3.697 | −2.206 | −10.605 | −4.335 | −5.559 |
| 518517 | 2 | −2.179 | −0.709 | 0.105 | 0.616 | −3.083 | −1.524 | | −3.362 | −4.381 |
| 548 | 2 | −1.985 | −0.989 | −0.096 | 1.032 | −3.003 | −1.643 | | −3.539 | −3.932 |
| 109.1 | 2 | −1.911 | −2.774 | −1.415 | 1.318 | −1.147 | −3.555 | | −4.008 | −3.872 |
| 104.1 | 2 | −2.027 | −1.977 | −0.509 | 1.549 | −3.334 | −1.876 | | −4.567 | −3.394 |
| 115.1 | 2 | −2.956 | −0.946 | −0.87 | 1.074 | −3.791 | −3.018 | −8.669 | −5.171 | −4.874 |
| 117.1 | 2 | −3.029 | −0.855 | −1.993 | 1.207 | −3.634 | −2.517 | −9.328 | −4.463 | −5.306 |
| 111.1 | 2 | −2.04 | −0.941 | −0.993 | 1.743 | −3.667 | −2.375 | −8.652 | −4.97 | −6.774 |
| 100.1 | 2 | −1.197 | −1.679 | −1.697 | 1.09 | −3.085 | −4.042 | −11.57 | −4.463 | −3.372 |
| 114.1 | 2 | −1.028 | −1.584 | −2.528 | 1.369 | −6.436 | −4.804 | −9.469 | −5.124 | −2.233 |
| 101.1 | 2 | −1.951 | −0.026 | −2.282 | 0.573 | −4.507 | −3.676 | −9.105 | −5.153 | −4.536 |

TABLE 7C

| Sample ID | Class | 19 hsa-miR-18b-5p | 20 hsa-miR-187-3p | 21 hsa-miR-186-5p | 22 hsa-miR-199a-5p | 23 hsa-miR-155-5p | 24 hsa-miR-454-3p | 25 hsa-miR-34a-5p | 26 hsa-miR-19b-3p | 27 hsa-miR-21-5p |
|---|---|---|---|---|---|---|---|---|---|---|
| | | miRNA prevalence by qRT-PCR | | | | | | | | |
| 231 | 1 | −0.081 | −7.289 | 0.012 | −2.856 | −1.224 | −1.865 | 2.882 | 4.815 | 6.548 |
| 305K | 1 | −0.756 | −10.548 | −1.062 | | −6.143 | −4.823 | 3.82 | 4.429 | 6.378 |
| 308 | 1 | −0.525 | −9.685 | −0.749 | | −4.398 | −2.696 | 3.558 | 3.926 | 6.747 |
| 355 | 1 | −0.657 | −4.43 | 0.484 | | −2.526 | −1.326 | 0.679 | 5.796 | 5.976 |
| 357 | 1 | −0.209 | −3.611 | −1.247 | −5.837 | −3.158 | −2.117 | 2.372 | 4.462 | 7.379 |
| 413 | 1 | −0.845 | −5.571 | −0.972 | | −6.811 | −3.884 | 3.327 | 4.405 | 5.824 |
| 453 | 1 | 0.406 | −1.641 | −0.844 | −1.063 | 0.807 | −4.025 | 2.791 | 4.666 | 6.767 |
| 463 | 1 | 0.629 | −0.571 | −0.231 | −6.178 | −2.299 | −3.065 | 3.128 | 4.194 | 7.741 |
| 42810 | 1 | −0.15 | −1.372 | −0.799 | −4.769 | −2.439 | −3.882 | 4.326 | | 5.99 |
| 42310 | 1 | −1.392 | −5.462 | −1 | −4.673 | −5.446 | −1.656 | 2.531 | 4.003 | 5.298 |
| 42910 | 1 | −0.291 | −5.851 | −0.389 | −7.413 | −3.818 | −2.186 | 1.871 | 4.804 | 7.155 |
| 52710 | 1 | 0.12 | −7.669 | −0.912 | −7.58 | −5.286 | −1.183 | 1.686 | 5.176 | 5.663 |
| 110 | 1 | 0.281 | −1.895 | −1.033 | −3.221 | −4.399 | −2.118 | 2.99 | 4.973 | 5.287 |
| 129 | 1 | 0.358 | −2.988 | −0.269 | −3.416 | −1.373 | −0.692 | 2.214 | 4.601 | 7.334 |
| 329SCC | 1 | 0.558 | −8.155 | −0.327 | −8.805 | −5.165 | −1.146 | 1.786 | 3.629 | 8.122 |
| 359 | 1 | 0.361 | −5.11 | −0.453 | −5.447 | −3.155 | −1.457 | 1.986 | 4.681 | 8.165 |
| 383 | 1 | 0.378 | −3.051 | −0.218 | −3.522 | −1.433 | −0.599 | 2.039 | 4.662 | 7.583 |
| 449 | 1 | 0.23 | −4.363 | 0.047 | −5.911 | −3.06 | −1.308 | 0.947 | 4.745 | 6.358 |
| 466 | 1 | 0.93 | −4.896 | −0.603 | −5.949 | −1.572 | −1.096 | 1.984 | 4.741 | 6.644 |
| 485 | 1 | 0.608 | −6.591 | 0.185 | −3.978 | −3.608 | −0.308 | 2.021 | 5.68 | 7.469 |
| 1019.2 | 2 | −2.401 | | −0.055 | | −4.766 | −4.37 | 3.112 | 4.608 | 2.804 |
| 1098 | 2 | −1.309 | | 0.105 | −7.091 | −4.631 | −1.859 | 2.11 | 4.779 | 4.471 |
| 28.2 | 2 | −0.153 | −6.653 | −0.582 | −9.007 | −4.545 | −1.998 | 3.705 | 4.394 | 5.515 |
| 1920.1 | 2 | −0.593 | −8.9 | 0.473 | | −6.196 | −3.765 | 4.649 | 5.36 | 5.579 |
| 426 | 2 | −0.395 | −6.184 | −1.274 | −5.489 | −3.524 | −4.896 | 3.534 | 4.429 | 4.037 |
| 514 | 2 | −1.493 | −11.691 | −1.109 | −9.314 | −6.339 | −3.128 | 3.517 | 3.454 | 5.115 |
| 515 | 2 | −0.229 | −7.705 | −0.857 | −6.241 | −4.589 | −3.419 | 3.842 | 4.162 | 6.25 |
| 518517 | 2 | −0.036 | −11.259 | −0.254 | | −4.032 | −2.412 | 4.238 | 4.451 | 7.036 |
| 548 | 2 | 0.054 | −8.328 | −0.293 | −9.742 | −3.598 | −2.437 | 4.333 | 4.467 | 6.155 |
| 109.1 | 2 | −1.051 | −5.177 | −0.335 | −6.109 | −5.165 | −2.773 | 3.112 | 3.511 | 6.984 |
| 104.1 | 2 | −0.165 | −7.268 | −0.597 | −8.711 | −6.52 | −2.733 | 3.33 | 3.526 | 5.912 |
| 115.1 | 2 | −0.802 | −8.239 | −3.692 | | −4.248 | −3.168 | 3.442 | 3.236 | 6.418 |
| 117.1 | 2 | −1.982 | −8.109 | −3.205 | −7.278 | −3.901 | −2.015 | 2.962 | 3.157 | 3.892 |
| 111.1 | 2 | −1.336 | | −3.673 | −8.019 | −6.77 | −3.596 | 3.87 | 3.524 | 5.155 |
| 100.1 | 2 | −1.735 | −6.034 | −3.978 | −12.015 | −5.019 | −5.004 | 3.993 | 2.796 | 4.836 |
| 114.1 | 2 | −2.103 | −6.308 | −3.707 | | −6.098 | −4.796 | 3.253 | 2.558 | 5.319 |
| 101.1 | 2 | 1.543- | −8.513 | −4.895 | | −7.015 | −4.942 | 2.516 | 4.984 | 4.902 |

TABLE 7D

| miRNA prevalence by qRT-PCR | | | | | | | | | | |
|---|---|---|---|---|---|---|---|---|---|---|
| Sample ID | Class | 28 hsa-miR-324-3p | 29 hsa-miR-19a-3p | 30 hsa-miR-150-5p | 31 hsa-let-7d-3p | 32 hsa-miR-671-5p | 33 hsa-miR-10b-5p | 34 hsa-miR-365a-3p | 35 hsa-miR-190a | 36 hsa-miR-17-5p |
| 231 | 1 | −0.336 | 2.958 | 0.429 | −1.397 | −6.556 | −2.351 | 2.367 | −7.055 | −3.503 |
| 305K | 1 | 0.625 | 2.495 | −5.214 | 0.097 | −6.139 | −9.92 | 3.482 | −10.1 | −3.035 |
| 308 | 1 | 0.011 | 2.591 | −2.764 | −1.049 | −7.946 | −1.198 | 2.818 | −11.295 | −3.661 |
| 355 | 1 | −0.617 | 4.446 | −1.676 | −0.319 | | | 1.293 | −7.339 | −2.982 |
| 357 | 1 | −1.804 | 2.991 | −2.434 | −3.149 | −8.005 | −1.837 | 1.904 | −6.01 | −3.138 |
| 413 | 1 | −0.295 | 2.672 | −3.928 | −1.311 | −5.963 | −5.337 | 2.183 | −8.882 | −2.883 |
| 453 | 1 | −0.004 | 2.611 | 4.359 | −1.206 | −5.063 | −0.09 | 1.322 | −7.893 | −3.959 |
| 463 | 1 | 0.229 | 3.328 | −2.218 | −1.579 | −5.702 | −0.455 | 3.223 | −10.821 | −3.23 |
| 42810 | 1 | 0.791 | 2.654 | −1.53 | −0.998 | −7.067 | −1.701 | 3.332 | | −3.055 |
| 42310 | 1 | −0.443 | 1.926 | −3.693 | −0.923 | −6.63 | −3.611 | 1.972 | −8.506 | −3.666 |
| 42910 | 1 | −0.77 | 3.386 | −1.43 | −0.878 | −9.192 | −5.827 | 2.309 | −8.061 | −2.959 |
| 52710 | 1 | −0.514 | 3.629 | −1.811 | −0.874 | −8.064 | −11.33 | 1.39 | −4.931 | −2.938 |
| 110 | 1 | −0.136 | 3.763 | −0.361 | −0.903 | −5.467 | −3.342 | 2.871 | −5.763 | −2.418 |
| 129 | 1 | −0.509 | 3.197 | 0.068 | −1.437 | −6.223 | −1.884 | 1.883 | −5.496 | −2.891 |
| 329SCC | 1 | −0.619 | 2.303 | −2.495 | −2.879 | −10.17 | −5.961 | 2.106 | −7.706 | −2.458 |
| 359 | 1 | −0.591 | 3.303 | −0.306 | −2.556 | | −3.697 | 2.314 | −6.591 | −2.314 |
| 383 | 1 | −0.612 | 3.217 | 0.134 | −1.477 | −5.994 | −1.188 | 1.902 | −5.112 | −2.445 |
| 449 | 1 | −0.612 | 3.54 | 0.715 | −1.133 | −7.33 | −3.446 | 1.235 | −5.432 | −2.968 |
| 466 | 1 | −0.297 | 3.596 | −0.047 | −1.254 | −5.455 | −3.81 | 1.831 | −6.764 | −2.292 |
| 485 | 1 | −0.365 | 4.566 | −0.504 | −2.623 | −8.238 | −3.518 | 1.517 | −3.443 | −2.102 |
| 1019.2 | 2 | 2.27 | 1.639 | −1.953 | 0.977 | −8.25 | | 2.389 | | −4.401 |
| 1098 | 2 | −0.312 | 3.485 | −2.472 | 0.414 | | | 1.73 | | −3.227 |
| 28.2 | 2 | 0.053 | 2.213 | −1.688 | −1.876 | −8.12 | −8.644 | 3.178 | | −2.438 |
| 1920.1 | 2 | 0.9 | 2.781 | −4.518 | −1.604 | −8.115 | −5.203 | 2.934 | −10.534 | −3.111 |
| 426 | 2 | 1.17 | 3.923 | 0.002 | −0.694 | −6.766 | −8.044 | 2.758 | −8.748 | −4.695 |
| 514 | 2 | 0.186 | 1.473 | −2.533 | −0.126 | | −10.346 | 2.638 | | −3.497 |
| 515 | 2 | 0.012 | 2.559 | −3.27 | −0.632 | −9.431 | −8.012 | 3.231 | −9.315 | −3.64 |
| 518517 | 2 | −0.172 | 2.846 | −5.942 | −1.307 | −6.64 | −9.029 | 2.949 | −8.979 | −3.358 |
| 548 | 2 | 0.48 | 2.489 | −3.162 | −1.771 | −7.321 | −13.634 | 3.515 | −8.985 | −2.78 |
| 109.1 | 2 | 0.965 | 2.381 | −1.994 | 0.73 | −10.022 | | 3.776 | | −3.676 |
| 104.1 | 2 | 0.929 | 2.849 | −1.68 | 0.659 | −9.482 | −10.441 | 2.985 | −11.71 | −2.763 |
| 115.1 | 2 | −0.331 | 1.489 | −2.948 | −0.72 | −10.069 | | 3.039 | −9.642 | −3.419 |
| 117.1 | 2 | 0.107 | 1.134 | −1.715 | −0.688 | −7.815 | | 2.309 | −10.344 | −4.134 |
| 111.1 | 2 | 0.387 | 1.704 | −3.4 | −0.975 | −9.612 | | 3.275 | −11.653 | −3.39 |
| 100.1 | 2 | 0.733 | 1.749 | −3.941 | 0.286 | −9.26 | | 3.313 | −13.018 | −3.912 |
| 114.1 | 2 | 0.428 | 0.627 | −4.969 | −0.086 | −9.404 | | 2.662 | | −3.64 |
| 101.1 | 2 | −0.858 | 1.925 | −4.937 | −1.639 | | | 2.174 | −9.961 | −4.321 |

TABLE 7E

| miRNA prevalence by qRT-PCR | | | | | | | | | | |
|---|---|---|---|---|---|---|---|---|---|---|
| Sample ID | Class | 37 hsa-miR-127-3p | 38 hsa-miR-135b-5p | 39 hsa-miR-196b-5p | 40 hsa-miR-296-5p | 41 hsa-miR-20b-5p | 42 hsa-miR-375 | 43 hsa-miR-345-5p | 44 hsa-miR-135a-5p | 45 hsa-miR-146b-5p |
| 231 | 1 | −6.514 | 0.716 | −7.231 | −6.398 | −8.052 | 3.97 | −10.586 | −3.263 | −3.609 |
| 305K | 1 | | 0.584 | | −4.104 | −11.347 | 5.068 | −8.193 | −2.601 | −3.922 |
| 308 | 1 | −9.022 | 0.63 | −9.933 | −4.631 | −10.395 | 4.355 | −8.357 | −2.627 | −4.205 |
| 355 | 1 | | −2.487 | −3.362 | −8.587 | | −1.286 | −7.459 | −4.762 | −2.845 |
| 357 | 1 | −6.242 | 0.27 | −5.261 | −7.621 | −7.779 | 1.185 | −8.8 | −2.913 | −4.393 |
| 413 | 1 | −6.746 | 0.65 | −8.147 | −4.071 | | 3.873 | −8.575 | −0.116 | −4.956 |
| 453 | 1 | −3.709 | −1.531 | −4.347 | −5.724 | −7.678 | 1.881 | −9.664 | −5.111 | −0.694 |
| 463 | 1 | −8.927 | 0.938 | −5.041 | −9.182 | −11.793 | 0.123 | −10.466 | −2.455 | −4.297 |
| 42810 | 1 | −7.441 | 1 | −7.613 | −7.486 | | 4.39 | −7.066 | −2.678 | −3.434 |
| 42310 | 1 | | −0.181 | −5.32 | −5.556 | −7.564 | 4.097 | −7.743 | −3.674 | −3.842 |
| 42910 | 1 | −9.015 | 1.861 | −6.521 | −6.035 | −8.729 | 3.841 | −9.482 | 0.208 | −3.49 |
| 52710 | 1 | | −0.879 | −5.413 | −4.352 | −5.94 | 3.033 | −9.54 | −4.456 | −4.157 |
| 110 | 1 | −4.577 | 1.64 | −3.779 | −5.768 | −10.054 | 3.158 | −8.588 | −2 | −3.697 |
| 129 | 1 | −5.575 | 0.371 | −4.252 | −8.205 | −6.272 | −0.048 | −7.364 | −3.598 | −2.167 |
| 329SCC | 1 | | 1.842 | −8.567 | −6.814 | −8.409 | 4.957 | −8.821 | −2.297 | −2.902 |
| 359 | 1 | −7.346 | 2.686 | −5.502 | −5.627 | −7.619 | 4.188 | −10.045 | 1.225 | −2.64 |
| 383 | 1 | −5.963 | 0.365 | −4.033 | −8.336 | −5.897 | 0.057 | −7.88 | −3.181 | −1.901 |
| 449 | 1 | −7.844 | −0.618 | −4.263 | −5.772 | −6.502 | 0.27 | −7.154 | −4.543 | −3.246 |
| 466 | 1 | −5.48 | 0.721 | −2.332 | −6.206 | −9.097 | 4.115 | −7.85 | −3.298 | −2.434 |
| 485 | 1 | −6.429 | −0.421 | −4.474 | −8.683 | −5.147 | 3.392 | −9.128 | −3.729 | −2.081 |
| 1019.2 | 2 | | −2.756 | −8.362 | −4.603 | | 4.97 | −7.138 | −5.385 | −5.079 |
| 1098 | 2 | | −3.081 | −4.641 | −6.167 | | 3.177 | −6.44 | −6.109 | −4.43 |

TABLE 7E-continued

| miRNA prevalence by qRT-PCR | | | | | | | | | | |
|---|---|---|---|---|---|---|---|---|---|---|
| Sample ID | Class | 37 hsa-miR-127-3p | 38 hsa-miR-135b-5p | 39 hsa-miR-196b-5p | 40 hsa-miR-296-5p | 41 hsa-miR-20b-5p | 42 hsa-miR-375 | 43 hsa-miR-345-5p | 44 hsa-miR-135a-5p | 45 hsa-miR-146b-5p |
| 28.2 | 2 | | −0.873 | −7.212 | −5.815 | −9.1 | 5.278 | −6.917 | −4.056 | −4.293 |
| 1920.1 | 2 | | 0.277 | | −3.816 | −12.874 | 5.425 | −8.606 | −3.044 | −3.567 |
| 426 | 2 | | −2.624 | −7.675 | | −10.697 | 4.854 | | −6.01 | −4.365 |
| 514 | 2 | | 0.063 | −7.464 | −4.805 | −9.178 | 4.553 | −9.803 | −3.617 | −5.469 |
| 515 | 2 | −8.771 | −0.099 | −6.788 | −5.126 | −10.439 | 3.875 | −10.518 | −3.269 | −4.373 |
| 518517 | 2 | −8.807 | 0.804 | | −5.35 | −9.398 | 4.142 | −10.573 | −3.242 | −4.321 |
| 548 | 2 | −13.752 | 0.94 | −10.093 | −3.936 | −9.871 | 5.211 | −10.929 | −3.028 | −4.08 |
| 109.1 | 2 | −7.388 | 0.547 | −5.815 | −4.113 | −10.675 | 4.607 | −7.795 | −3.664 | −4.627 |
| 104.1 | 2 | | 0.1 | −6.543 | −4.464 | −10.903 | 5.459 | −6.948 | −3.08 | −3.134 |
| 115.1 | 2 | −9.163 | −1.042 | −6.575 | −6.675 | −11.557 | 3.301 | −2.144 | −4.148 | −4.701 |
| 117.1 | 2 | −8.187 | −2.117 | −3.919 | −4.231 | −9.619 | 2.888 | −0.713 | −5.569 | −4.527 |
| 111.1 | 2 | −9.663 | −1.305 | −7.129 | −4.224 | −11.985 | 3.83 | −2.559 | −4.163 | −4.642 |
| 100.1 | 2 | −10.253 | −1.268 | −9.286 | −3.973 | −8.573 | 5.179 | −2.364 | −4.521 | −5.543 |
| 114.1 | 2 | | −1.747 | −12.104 | −4.13 | −12.087 | 5.06 | −1.858 | −4.544 | −5.972 |
| 101.1 | 2 | | −0.718 | −11.954 | −5.311 | −12.145 | 4.062 | −1.894 | −3.863 | −5.397 |

TABLE 7F

| miRNA prevalence by qRT-PCR | | | | | | | |
|---|---|---|---|---|---|---|---|
| Sample ID | Class | 46 hsa-miR-142-3p | 47 hsa-miR-106a-5p | 48 hsa-miR-100-5p | 49 hsa-miR-340-5p | 50 hsa-miR-146a-5p | 51 hsa-miR-31-5p |
| 231 | 1 | 1.916 | 2.946 | −0.812 | | −0.995 | 0.23 |
| 305K | 1 | −1.046 | 3.142 | −3.422 | −11.566 | −3.69 | 1.343 |
| 308 | 1 | 0.837 | 2.743 | −2.599 | | −3.473 | 3.06 |
| 355 | 1 | 6.058 | 2.973 | −0.182 | | −1.482 | −1.294 |
| 357 | 1 | 3.426 | 2.747 | −0.889 | −9.05 | −1.142 | 2.468 |
| 413 | 1 | 1.571 | 2.891 | −1.219 | | −5.096 | 1.49 |
| 453 | 1 | 3.134 | 3.371 | −0.455 | | 2.632 | 2.587 |
| 463 | 1 | 2.371 | 3.919 | 0.372 | −11.646 | −0.179 | 3.479 |
| 42810 | 1 | 0.635 | 3.503 | −0.533 | | −0.697 | 2.147 |
| 42310 | 1 | 2.477 | 2.541 | −1.619 | | −3.331 | 0.537 |
| 42910 | 1 | 4.146 | 3.347 | −1.614 | −11.886 | −1.654 | 3.974 |
| 52710 | 1 | 3.927 | 3.321 | −2.838 | | −3.627 | 0.028 |
| 110 | 1 | 2.956 | 3.649 | 0.027 | | −0.496 | 3.805 |
| 129 | 1 | 4.174 | 3.578 | 0.214 | −12.308 | −0.039 | 4.03 |
| 329SCC | 1 | 1.91 | 3.724 | −1.993 | −14.897 | −3.564 | 1.117 |
| 359 | 1 | 2.882 | 3.71 | 0.213 | −12.614 | −0.791 | 4.356 |
| 383 | 1 | 4.139 | 3.513 | 0.217 | −10.866 | −0.075 | 4.086 |
| 449 | 1 | 4.672 | 3.394 | −0.736 | −11.531 | −0.643 | 2.295 |
| 466 | 1 | 3.174 | 3.774 | −1.348 | −12.371 | −0.64 | 2.598 |
| 485 | 1 | 4.188 | 4.042 | −2.393 | −12.313 | −1.03 | 2.857 |
| 1019.2 | 2 | 0.397 | 1.968 | −1.709 | | −2.648 | 0.566 |
| 1098 | 2 | 5.185 | 2.147 | −5.117 | −7.704 | −3.206 | 0.046 |
| 28.2 | 2 | 2.657 | 3.385 | −2.33 | −10.572 | −3.282 | −1.88 |
| 1920.1 | 2 | −1.563 | 3.101 | −1.932 | −13.003 | −4.669 | −2.013 |
| 426 | 2 | 0.879 | 2.863 | −1.071 | | −2.846 | −4.373 |
| 514 | 2 | 1.414 | 2.21 | −1.99 | −12.81 | −2.529 | −1.3 |
| 515 | 2 | 0.805 | 2.906 | −1.488 | | −0.632 | −0.075 |
| 518517 | 2 | −0.818 | 3.026 | −2.265 | | −2.519 | 0.457 |
| 548 | 2 | −0.563 | 3.596 | −1.427 | −11.738 | −4.365 | −0.952 |
| 109.1 | 2 | 2.082 | 3.769 | −1.545 | | −0.714 | 2.895 |
| 104.1 | 2 | 3.523 | 3.698 | −2.463 | | −2.648 | 2.33 |
| 115.1 | 2 | 2.076 | 2.829 | −3.143 | −4.134 | −0.958 | 1.927 |
| 117.1 | 2 | 3.466 | 2.222 | −3.322 | −4.058 | −3.827 | 1.1 |
| 111.1 | 2 | 0.492 | 3.038 | −2.881 | −3.727 | −6.389 | 0.79 |
| 100.1 | 2 | −1.128 | 2.698 | −3.421 | −5.061 | −3.76 | 1.171 |
| 114.1 | 2 | 0.498 | 2.261 | −5.999 | −3.916 | −5.52 | −0.6 |
| 101.1 | 2 | 1.741 | 1.553 | −6.997 | −3.836 | −3.88 | 0.602 |

A comparison between the miRNA sequences differentially expressed in the TCGA data examined and the miRNA sequences identified by application of qRT-PCR to brush cytology samples yielded some overlap with 17 showing similar differential expression. In this regard, the TCGA data was obtained from surgical samples containing a combination of tumor and stromal tissue while the brush cytology samples examined by qRT-PCR were essentially cells from the epithelium. Direct comparison between the two datasets is made difficult by the lack of unambiguous labeling of the miRNAs from the TCGA dataset.

A statistical study of the qRT-PCR data obtained from the brush cytology samples was initiated to determine which miRNA sequences were most helpful in building an OSCC classifier. One approach was to simply apply selected tools in the BRB-Array Tools suit and the other was to overlay the Greedy Pairs approach described in "New feature subset selection procedures for classification of expression profiles" by Bo et al in Genome Biology 3(4) Pages 1-11 (2002) with the BRB-Array Tools. In the former case significance levels of 0.0001, 0.0003 and 0.001 were selected and the tool determined the 7, 13 and 24 sequences, respectively, that were needed, while in the latter case 3, 5 and 10 miRNA pairs were selected. The former approach yielded the results resorted in Tables 8, 9 & 10 while the latter approach yielded the results reported in Tables 11, 12 & 13. In the Tables Class label 1 refers to OSCC samples while Class label 2 refers to controls.

TABLE 8

7 Sequence Classifier

| | Sample ID | Class Label | Mean # of Genes in Classifier | Compound Covariate Predictor Correct | Diagonal Linear Discriminant Analysis Correct | 1-Nearest Neighbor Correct | 3-Nearest Neighbor Correct | Nearest Centroid Correct | Support Vector Machine Correct | BAYESIAN Compound Covariate Predictor Correct |
|---|---|---|---|---|---|---|---|---|---|---|
| 1 | 231 | 1 | 6 | YES | YES | YES | YES | YES | YES | YES |
| 2 | 305 | 1 | 10 | NO | NO | NO | NO | NO | NO | NO |
| 3 | 308 | 1 | 6 | NO | NO | NO | NO | NO | NO | NO |
| 4 | 355 | 1 | 8 | YES | YES | NO | NO | NO | YES | NA |
| 5 | 357 | 1 | 5 | YES | YES | YES | YES | YES | YES | YES |
| 6 | 413 | 1 | 9 | NO | NO | NO | NO | NO | NO | NO |
| 7 | 453 | 1 | 5 | YES | YES | YES | YES | YES | YES | YES |
| 8 | 463 | 1 | 7 | NO | NO | NO | NO | NO | NO | NO |
| 9 | 4281 | 1 | 6 | NO | NO | NO | NO | NO | NO | NO |
| 10 | 4231 | 1 | 8 | YES | YES | YES | YES | YES | YES | YES |
| 11 | 4291 | 1 | 5 | YES | YES | NO | NO | NO | YES | NA |
| 12 | 5271 | 1 | 7 | YES | YES | YES | NO | YES | YES | NA |
| 13 | 110 | 1 | 6 | YES | YES | YES | YES | YES | YES | YES |
| 14 | 129 | 1 | 5 | YES | YES | YES | YES | YES | YES | YES |
| 15 | 329 | 1 | 5 | YES | YES | YES | YES | YES | YES | YES |
| 16 | 359 | 1 | 5 | YES | YES | YES | YES | YES | YES | YES |
| 17 | 383 | 1 | 5 | YES | YES | YES | YES | YES | YES | YES |
| 18 | 449 | 1 | 6 | YES | YES | YES | YES | YES | YES | YES |
| 19 | 466 | 1 | 5 | YES | YES | YES | YES | YES | YES | YES |
| 20 | 485 | 1 | 5 | YES | YES | YES | YES | YES | YES | YES |
| 21 | 1019.2 | 2 | 5 | YES | YES | YES | YES | YES | YES | YES |
| 22 | 1098 | 2 | 5 | NO | NO | NO | NO | NO | NO | NO |
| 23 | 28.2 | 2 | 8 | YES | NO | NO | NO | YES | NO | NA |
| 24 | 1920.1 | 2 | 8 | YES | YES | YES | YES | YES | YES | YES |
| 25 | 426 | 2 | 7 | YES | YES | YES | YES | YES | YES | YES |
| 26 | 514 | 2 | 5 | YES | YES | YES | YES | YES | YES | YES |
| 27 | 515 | 2 | 7 | YES | YES | YES | YES | YES | YES | YES |
| 28 | 518517 | 2 | 7 | NO | NO | NO | NO | NO | NO | NA |
| 29 | 548 | 2 | 7 | NO | YES | YES | NO | NO | NO | NA |
| 30 | 109.1 | 2 | 6 | YES | YES | YES | YES | NO | YES | NA |
| 31 | 104.1 | 2 | 7 | YES | YES | YES | YES | YES | YES | YES |
| 32 | 115.1 | 2 | 6 | YES | YES | YES | YES | YES | NO | YES |
| 33 | 117.1 | 2 | 5 | YES | YES | YES | NO | YES | NO | YES |
| 34 | 111.1 | 2 | 5 | YES | YES | YES | YES | YES | YES | YES |
| 35 | 100.1 | 2 | 5 | YES | YES | YES | YES | YES | YES | YES |
| 36 | 114.1 | 2 | 5 | YES | YES | YES | YES | YES | YES | YES |
| 37 | 101.1 | 2 | 4 | YES | YES | YES | YES | YES | YES | YES |
| 38 | 112.1 | 2 | 6 | YES | YES | YES | YES | YES | YES | YES |
| % Correctly Classified | | | | 74 | 79 | 76 | 63 | 68 | 76 | 84 |

Note:

NA denotes the sample is unclassified. These samples are excluded in the computation of the mean percent of correct classification.

TABLE 9

13 Sequence Classifier

| | Sample ID | Class Label | Mean # of Genes in Classifier | Compound Covariate Predictor Correct | Diagonal Linear Discriminant Analysis Correct | 1-Nearest Neighbor Correct | 3-Nearest Neighbor Correct | Nearest Centroid Correct | Support Vector Machine Correct | BAYESIAN Compound Covariate Predictor Correct |
|---|---|---|---|---|---|---|---|---|---|---|
| 1 | 231 | 1 | 10 | YES | YES | YES | YES | YES | YES | YES |
| 2 | 305 | 1 | 17 | NO | NO | NO | NO | NO | NO | NO |
| 3 | 308 | 1 | 14 | NO | NO | YES | YES | NO | YES | NO |
| 4 | 355 | 1 | 10 | No | YES | NO | NO | NO | YES | NA |
| 5 | 357 | 1 | 9 | YES | YES | YES | YES | YES | YES | YES |
| 6 | 413 | 1 | 16 | NO | NO | NO | NO | NO | YES | NO |
| 7 | 453 | 1 | 10 | YES | YES | YES | YES | YES | YES | YES |
| 8 | 463 | 1 | 11 | YES | YES | YES | YES | YES | YES | YES |
| 9 | 4281 | 1 | 12 | NO | NO | YES | NO | YES | YES | NA |
| 10 | 4231 | 1 | 12 | YES | YES | YES | YES | YES | YES | YES |
| 11 | 4291 | 1 | 11 | YES | YES | NO | NO | NO | NO | NA |
| 12 | 5271 | 1 | 11 | YES | YES | YES | NO | YES | YES | NA |
| 13 | 110 | 1 | 9 | YES | YES | YES | YES | YES | YES | YES |
| 14 | 129 | 1 | 8 | YES | YES | YES | YES | YES | YES | YES |
| 15 | 329 | 1 | 14 | YES | YES | YES | YES | YES | YES | YES |
| 16 | 359 | 1 | 9 | YES | YES | YES | YES | YES | YES | YES |
| 17 | 383 | 1 | 8 | YES | YES | YES | YES | YES | YES | YES |
| 18 | 449 | 1 | 8 | YES | YES | YES | YES | YES | YES | YES |
| 19 | 466 | 1 | 11 | YES | YES | YES | YES | YES | YES | YES |
| 20 | 485 | 1 | 10 | YES | YES | YES | YES | YES | YES | YES |
| 21 | 1019.2 | 2 | 8 | YES | YES | YES | YES | YES | YES | YES |
| 22 | 1098 | 2 | 9 | NO | NO | NO | NO | NO | NO | NA |
| 23 | 28.2 | 2 | 12 | YES | NO | YES | YES | YES | YES | NA |
| 24 | 1920.1 | 2 | 12 | YES | NO | NO | NO | YES | YES | NA |
| 25 | 426 | 2 | 12 | YES | YES | YES | YES | YES | YES | YES |
| 26 | 514 | 2 | 11 | YES | YES | YES | NO | YES | YES | YES |
| 27 | 515 | 2 | 12 | YES | YES | YES | YES | YES | YES | YES |
| 28 | 518517 | 2 | 14 | YES | NO | YES | YES | YES | YES | NA |
| 29 | 548 | 2 | 13 | NO | NO | YES | YES | NO | YES | NA |
| 30 | 109.1 | 2 | 10 | NO | YES | YES | NO | NO | NO | NA |
| 31 | 104.1 | 2 | 11 | YES | YES | YES | YES | YES | YES | YES |
| 32 | 115.1 | 2 | 11 | YES | YES | YES | YES | YES | YES | YES |
| 33 | 117.1 | 2 | 9 | YES | YES | YES | YES | YES | YES | YES |
| 34 | 111.1 | 2 | 8 | YES | YES | YES | YES | YES | YES | YES |
| 35 | 100.1 | 2 | 9 | YES | YES | YES | YES | YES | YES | YES |
| 36 | 114.1 | 2 | 8 | YES | YES | NO | NO | YES | NO | YES |
| 37 | 101.1 | 2 | 8 | YES | YES | YES | YES | YES | YES | YES |
| 38 | 112.1 | 2 | 9 | YES | YES | YES | YES | YES | YES | YES |
| % Correctly Classified | | | | 79 | 76 | 82 | 74 | 79 | 87 | 89 |

Note:
NA denotes the sample is unclassified. These samples are excluded in the computation of the mean percent of correct classification.

TABLE 10

24 Sequence Classifier

| | Sample ID | Class Label | Mean # of Genes in Classifier | Compound Covariate Predictor Correct | Diagonal Linear Discriminant Analysis Correct | 1-Neareast Neighbor Correct | 3-Neareast Neighbor Correct | Nearest Centroid Correct | Support Vector Machine Correct | BAYESIAN Compound Covariate Predictor Correct |
|---|---|---|---|---|---|---|---|---|---|---|
| 1 | 231 | 1 | 24 | YES | YES | YES | YES | YES | YES | YES |
| 2 | 305 | 1 | 28 | NO | NO | NO | NO | NO | NO | NO |
| 3 | 308 | 1 | 27 | NO | NO | NO | YES | NO | YES | NO |
| 4 | 355 | 1 | 15 | NO | YES | NO | NO | NO | NO | NA |
| 5 | 357 | 1 | 18 | YES | YES | YES | YES | YES | YES | YES |
| 6 | 413 | 1 | 24 | NO | NO | NO | NO | NO | NO | NO |
| 7 | 453 | 1 | 23 | YES | YES | YES | YES | YES | YES | YES |
| 8 | 463 | 1 | 25 | YES | NO | NO | YES | YES | YES | NA |
| 9 | 4281 | 1 | 22 | NO | YES | NO | YES | YES | NO | NA |
| 10 | 4231 | 1 | 22 | YES | YES | YES | YES | YES | YES | YES |
| 11 | 4291 | 1 | 21 | YES | YES | YES | NO | YES | YES | NA |
| 12 | 5271 | 1 | 18 | YES | YES | YES | YES | YES | YES | YES |
| 13 | 110 | 1 | 22 | YES | YES | YES | YES | YES | YES | YES |

TABLE 10-continued

24 Sequence Classifier

| | Sample ID | Class Label | Mean # of Genes in Classifier | Compound Covariate Predictor Correct | Diagonal Linear Discriminant Analysis Correct | 1-Neareast Neighbor Correct | 3-Neareast Neighbor Correct | Nearest Centroid Correct | Support Vector Machine Correct | BAYESIAN Compound Covariate Predictor Correct |
|---|---|---|---|---|---|---|---|---|---|---|
| 14 | 129 | 1 | 16 | YES | YES | YES | YES | YES | YES | YES |
| 15 | 329 | 1 | 22 | YES | YES | YES | YES | YES | YES | YES |
| 16 | 359 | 1 | 21 | YES | YES | YES | YES | YES | YES | YES |
| 17 | 383 | 1 | 16 | YES | YES | YES | YES | YES | YES | YES |
| 18 | 449 | 1 | 17 | YES | YES | YES | YES | YES | YES | YES |
| 19 | 466 | 1 | 19 | YES | YES | YES | YES | YES | YES | YES |
| 20 | 485 | 1 | 17 | YES | YES | YES | YES | YES | YES | YES |
| 21 | 1019.2 | 2 | 14 | YES | YES | YES | YES | YES | YES | YES |
| 22 | 1098 | 2 | 23 | NO | NO | YES | YES | YES | NO | NA |
| 23 | 28.2 | 2 | 23 | YES | NO | YES | YES | YES | YES | NA |
| 24 | 1920.1 | 2 | 19 | YES | YES | YES | YES | YES | YES | YES |
| 25 | 426 | 2 | 19 | YES | YES | YES | YES | YES | YES | YES |
| 26 | 514 | 2 | 18 | YES | YES | YES | YES | YES | YES | YES |
| 27 | 515 | 2 | 23 | YES | YES | YES | YES | YES | YES | NA |
| 28 | 518517 | 2 | 22 | NO | NO | YES | YES | YES | NO | NA |
| 29 | 548 | 2 | 22 | NO | YES | NO | YES | YES | YES | YES |
| 30 | 109.1 | 2 | 19 | NO | YES | YES | NO | NO | NO | NA |
| 31 | 104.1 | 2 | 19 | YES | YES | YES | YES | YES | YES | YES |
| 32 | 115.1 | 2 | 18 | YES | YES | YES | YES | YES | YES | YES |
| 33 | 117.1 | 2 | 23 | YES | YES | YES | YES | YES | YES | YES |
| 34 | 111.1 | 2 | 18 | YES | YES | YES | YES | YES | YES | YES |
| 35 | 100.1 | 2 | 15 | YES | YES | YES | YES | YES | YES | YES |
| 36 | 114.1 | 2 | 16 | YES | YES | YES | YES | YES | NO | YES |
| 37 | 101.1 | 2 | 19 | YES | YES | YES | YES | YES | YES | YES |
| 38 | 112.1 | 2 | 19 | YES | YES | YES | YES | YES | YES | YES |
| | % Correctly Classified | | | 76 | 79 | 87 | 87 | 87 | 82 | 89 |

Note:
NA denotes the sample is unclassified. These samples are excluded in the computation of the mean percent of correct classification.

TABLE 11

3 Greedy Pairs

| | Sample ID | Class Label | Mean # of Genes in Classifier | Compound Covariate Predictor Correct | DLDA Correct | 1-Nearest Neighbor Correct | 3-Nearest Neighbor Correct | Nearest Centroid Correct | Support Vector Machine | BAYESIAN Compound Covariate Predictor Correct |
|---|---|---|---|---|---|---|---|---|---|---|
| 1 | 231 | 1 | 6 | YES | YES | YES | YES | YES | YES | YES |
| 2 | 305 | 1 | 5 | NO | NO | NO | NO | NO | NO | NO |
| 3 | 308 | 1 | 4 | NO | NO | NO | NO | NO | NO | NO |
| 4 | 355 | 1 | 5 | YES | YES | NO | NO | NO | NO | NA |
| 5 | 357 | 1 | 6 | YES | YES | YES | YES | YES | YES | YES |
| 6 | 413 | 1 | 6 | NO | NO | NO | NO | NO | NO | NO |
| 7 | 453 | 1 | 6 | YES | YES | YES | YES | YES | YES | YES |
| 8 | 463 | 1 | 6 | YES | NO | YES | YES | YES | YES | NA |
| 9 | 4281 | 1 | 5 | NO | NO | NO | NO | NO | NO | NA |
| 10 | 4231 | 1 | 6 | YES | YES | YES | YES | YES | YES | YES |
| 11 | 4291 | 1 | 6 | YES | YES | NO | YES | NO | YES | NA |
| 12 | 5271 | 1 | 6 | YES | YES | YES | NO | YES | YES | YES |
| 13 | 110 | 1 | 6 | YES | YES | YES | YES | YES | YES | YES |
| 14 | 129 | 1 | 6 | YES | YES | YES | YES | YES | YES | YES |
| 15 | 329 | 1 | 6 | YES | YES | YES | YES | YES | YES | YES |
| 16 | 359 | 1 | 6 | YES | YES | YES | YES | YES | YES | YES |
| 17 | 383 | 1 | 6 | YES | YES | YES | YES | YES | YES | YES |
| 18 | 449 | 1 | 6 | YES | YES | YES | YES | YES | YES | YES |
| 19 | 466 | 1 | 6 | YES | YES | YES | YES | YES | YES | YES |
| 20 | 485 | 1 | 6 | YES | YES | YES | YES | YES | YES | YES |
| 21 | 1019.2 | 2 | 5 | YES | YES | YES | YES | YES | YES | YES |
| 22 | 1098 | 2 | 4 | NO | NO | NO | NO | NO | NO | NO |
| 23 | 28.2 | 2 | 6 | YES | YES | YES | NO | YES | NO | YES |
| 24 | 1920.1 | 2 | 5 | YES | YES | NO | NO | YES | YES | YES |
| 25 | 426 | 2 | 6 | YES | YES | YES | YES | YES | YES | YES |
| 26 | 514 | 2 | 6 | YES | YES | YES | YES | YES | YES | YES |
| 27 | 515 | 2 | 6 | YES | YES | YES | YES | YES | YES | YES |
| 28 | 518517 | 2 | 6 | NO | NO | NO | NO | YES | NO | NA |

TABLE 11-continued

| | 3 Greedy Pairs | | | | | | | | | |
|---|---|---|---|---|---|---|---|---|---|---|
| | Sample ID | Class Label | Mean # of Genes in Classifier | Compound Covariate Predictor Correct | DLDA Correct | 1-Nearest Neighbor Correct | 3-Nearest Neighbor Correct | Nearest Centroid Correct | Support Vector Machine | BAYESIAN Compound Covariate Predictor Correct |
| 29 | 548 | 2 | 6 | NO | NO | NO | NO | NO | NO | NA |
| 30 | 109.1 | 2 | 6 | NO | NO | NO | NO | NO | NO | NO |
| 31 | 104.1 | 2 | 6 | YES | YES | YES | YES | YES | YES | YES |
| 32 | 115.1 | 2 | 5 | YES | YES | YES | YES | YES | YES | YES |
| 33 | 117.1 | 2 | 6 | YES | YES | YES | YES | YES | YES | YES |
| 34 | 111.1 | 2 | 5 | YES | YES | YES | YES | YES | YES | YES |
| 35 | 100.1 | 2 | 6 | YES | YES | YES | YES | YES | YES | YES |
| 36 | 114.1 | 2 | 5 | YES | YES | YES | YES | YES | YES | YES |
| 37 | 101.1 | 2 | 4 | YES | YES | YES | YES | YES | YES | YES |
| 38 | 112.1 | 2 | 5 | YES | YES | YES | YES | YES | YES | YES |
| | % Correctly Classified | | | 79 | 82 | 71 | 68 | 76 | 74 | 84 |

Note:
NA denotes the sample is unclassified. These samples are excluded in the computation of the mean percent of correct classification.

TABLE 12

| | 5 Greedy Pairs | | | | | | | | | |
|---|---|---|---|---|---|---|---|---|---|---|
| | Sample ID | Class Label | Mean # of Genes in Classifier | Compound Covariate Predictor Correct | DLDA Correct | 1-Nearest Neighbor Correct | 3-Nearest Neighbor Correct | Nearest Centroid Correct | Support Vector Machine | BAYESIAN Compound Covariate Predictor Correct |
| 1 | 231 | 1 | 10 | YES | YES | YES | YES | YES | YES | YES |
| 2 | 305 | 1 | 9 | NO | NO | NO | NO | NO | NO | NO |
| 3 | 308 | 1 | 8 | NO | NO | YES | YES | NO | YES | NO |
| 4 | 355 | 1 | 8 | NO | YES | NO | NO | NO | YES | NA |
| 5 | 357 | 1 | 10 | YES | YES | YES | YES | YES | YES | YES |
| 6 | 413 | 1 | 10 | NO | NO | NO | NO | NO | YES | NO |
| 7 | 453 | 1 | 10 | YES | YES | YES | YES | YES | YES | YES |
| 8 | 463 | 1 | 10 | YES | YES | YES | YES | YES | YES | YES |
| 9 | 4281 | 1 | 9 | NO | NO | YES | YES | YES | YES | NA |
| 10 | 4231 | 1 | 10 | YES | YES | YES | YES | YES | YES | YES |
| 11 | 4291 | 1 | 10 | YES | YES | NO | NO | NO | NO | NA |
| 12 | 5271 | 1 | 10 | YES | YES | YES | NO | YES | YES | NA |
| 13 | 110 | 1 | 10 | YES | YES | YES | YES | YES | YES | YES |
| 14 | 129 | 1 | 10 | YES | YES | YES | YES | YES | YES | YES |
| 15 | 329 | 1 | 9 | YES | YES | YES | YES | YES | YES | YES |
| 16 | 359 | 1 | 10 | YES | YES | YES | YES | YES | YES | YES |
| 17 | 383 | 1 | 10 | YES | YES | YES | YES | YES | YES | YES |
| 18 | 449 | 1 | 10 | YES | YES | YES | YES | YES | YES | YES |
| 19 | 466 | 1 | 10 | YES | YES | YES | YES | YES | YES | YES |
| 20 | 485 | 1 | 10 | YES | YES | YES | YES | YES | YES | YES |
| 21 | 1019.2 | 2 | 7 | YES | YES | YES | YES | YES | YES | YES |
| 22 | 1098 | 2 | 8 | NO | NO | NO | NO | NO | NO | NA |
| 23 | 28.2 | 2 | 10 | YES | NO | YES | YES | YES | YES | YES |
| 24 | 1920.1 | 2 | 8 | YES | YES | YES | YES | YES | YES | YES |
| 25 | 426 | 2 | 10 | YES | YES | YES | YES | YES | YES | YES |
| 26 | 514 | 2 | 10 | YES | YES | YES | NO | YES | YES | YES |
| 27 | 515 | 2 | 10 | YES | YES | YES | YES | YES | YES | YES |
| 28 | 518517 | 2 | 10 | YES | NO | YES | YES | YES | YES | NA |
| 29 | 548 | 2 | 10 | NO | NO | YES | YES | NO | YES | NA |
| 30 | 109.1 | 2 | 10 | NO | YES | YES | NO | NO | NO | NA |
| 31 | 104.1 | 2 | 10 | YES | YES | YES | YES | YES | YES | YES |
| 32 | 115.1 | 2 | 9 | YES | YES | YES | YES | YES | YES | YES |
| 33 | 117.1 | 2 | 9 | YES | YES | YES | NO | YES | YES | YES |
| 34 | 111.1 | 2 | 8 | YES | YES | YES | YES | YES | YES | YES |
| 35 | 100.1 | 2 | 9 | YES | YES | YES | YES | YES | YES | YES |
| 36 | 114.1 | 2 | 7 | YES | YES | NO | NO | YES | NO | YES |
| 37 | 101.1 | 2 | 7 | YES | YES | YES | YES | YES | YES | YES |
| 38 | 112.1 | 2 | 8 | YES | YES | YES | YES | YES | YES | YES |
| % Correct Classified | | | | 74 | 79 | 76 | 63 | 68 | 76 | 84 |

Note:
NA denotes the sample is unclassified. These samples are excluded in the computation of the mean percent of correct classification.

TABLE 13

| | 10 Greedy Pairs | | | | | | | | | |
|---|---|---|---|---|---|---|---|---|---|---|
| | Sample ID | Class Label | Mean # of Genes in Classifier | Compound Covariate Predictor Correct | DLDA Correct | 1-Nearest Neighbor Correct | 3-Nearest Neighbor Correct | Nearest Centroid Correct | Support Vector Machine | BAYESIAN Compound Covariate Predictor Correct |
| 1 | 231 | 1 | 19 | YES | YES | YES | YES | YES | YES | YES |
| 2 | 305 | 1 | 19 | NO | NO | NO | NO | NO | NO | NO |
| 3 | 308 | 1 | 18 | NO | NO | YES | YES | NO | YES | NO |
| 4 | 355 | 1 | 16 | NO | YES | NO | NO | NO | NO | NO |
| 5 | 357 | 1 | 19 | YES | YES | YES | YES | YES | YES | YES |
| 6 | 413 | 1 | 19 | NO | NO | NO | NO | NO | NO | NO |
| 7 | 453 | 1 | 20 | YES | YES | YES | YES | YES | YES | YES |
| 8 | 463 | 1 | 20 | YES | YES | YES | YES | YES | YES | NA |
| 9 | 4281 | 1 | 17 | NO | NO | YES | YES | YES | YES | YES |
| 10 | 4231 | 1 | 20 | YES | YES | YES | YES | YES | YES | YES |
| 11 | 4291 | 1 | 20 | YES | YES | NO | YES | YES | YES | YES |
| 12 | 5271 | 1 | 18 | YES | YES | YES | NO | YES | YES | YES |
| 13 | 110 | 1 | 18 | YES | YES | YES | YES | YES | YES | YES |
| 14 | 129 | 1 | 19 | YES | YES | YES | YES | YES | YES | YES |
| 15 | 329 | 1 | 19 | YES | YES | YES | YES | YES | YES | YES |
| 16 | 359 | 1 | 20 | YES | YES | YES | YES | YES | YES | YES |
| 17 | 383 | 1 | 20 | YES | YES | YES | YES | YES | YES | YES |
| 18 | 449 | 1 | 20 | YES | YES | YES | YES | YES | YES | YES |
| 19 | 466 | 1 | 20 | YES | YES | YES | YES | YES | YES | YES |
| 20 | 485 | 1 | 20 | YES | YES | YES | YES | YES | YES | YES |
| 21 | 1019.2 | 2 | 14 | YES | YES | YES | YES | YES | YES | YES |
| 22 | 1098 | 2 | 14 | YES | NO | NO | YES | YES | YES | NA |
| 23 | 28.2 | 2 | 19 | YES | NO | YES | YES | YES | YES | YES |
| 24 | 1920.1 | 2 | 17 | YES | YES | YES | YES | YES | YES | YES |
| 25 | 426 | 2 | 20 | YES | YES | YES | YES | YES | YES | YES |
| 26 | 514 | 2 | 18 | YES | YES | YES | YES | YES | NO | YES |
| 27 | 515 | 2 | 20 | YES | YES | YES | YES | YES | YES | YES |
| 28 | 518517 | 2 | 19 | NO | NO | NO | NO | YES | NO | NA |
| 29 | 548 | 2 | 19 | YES | YES | YES | YES | NO | YES | NA |
| 30 | 109.1 | 2 | 18 | NO | YES | YES | NO | NO | NO | NA |
| 31 | 104.1 | 2 | 19 | YES | YES | YES | YES | YES | YES | YES |
| 32 | 115.1 | 2 | 16 | YES | YES | YES | YES | YES | YES | YES |
| 33 | 117.1 | 2 | 19 | YES | YES | YES | NO | YES | YES | YES |
| 34 | 111.1 | 2 | 17 | YES | YES | YES | YES | YES | YES | YES |
| 35 | 100.1 | 2 | 19 | YES | YES | YES | YES | YES | YES | YES |
| 36 | 114.1 | 2 | 16 | YES | YES | YES | YES | YES | NO | YES |
| 37 | 101.1 | 2 | 17 | YES | YES | YES | YES | YES | YES | YES |
| 38 | 112.1 | 2 | 15 | YES | YES | YES | YES | YES | YES | YES |
| % Correctly Classified | | | | 82 | 82 | 84 | 87 | 84 | 82 | 88 |

Note:
NA denotes the sample is unclassified. These samples are excluded in the computation of the mean percent of correct classification.

The sequences utilized by each approach are reported in Table 14. A number of sequences are utilized by more than approach and some are utilized by all six. It is expected that any classifier, even if constructed using a different statistical treatment will make use of these conserved miRNA sequences.

TABLE 14

| | miRNA Sequence for Classifiers | | | | | |
|---|---|---|---|---|---|---|
| | Greedy Pairs Approach | | | Standard BRB-Array Tools Approach | | |
| | 6 | 10 | 20 | 5 | 13 | 24 |
| 1 | hsa-miR-130-3p | hsa-miR-130b-3p | hsa-miR-130b-3p | hsa-miR-130b-3p | hsa-miR-130b-3p | hsa-miR-130b-3p |
| 2 | hsa-miR-7-5p | hsa-mir-7-5p | hsa-mir-7-5p | hsa-miR-7-5p | hsa-miR-7-5p | hsa-mir-7-5p |
| 3 | hsa-miR-101-3p | hsa-miR-101-3p | hsa-miR-101-3p | hsa-miR-101-3p | hsa-miR-101-3p | hsa-miR-101-3p |
| 4 | hsa-miR-146b-5p | hsa-miR-146b-5p | hsa-miR-146b-5p | hsa-miR-146b-5p | hsa-miR-146b-5b | hsa-miR-146b-5p |
| 5 | hsa-miR-486-5p | hsa-miR-486-5p | hsa-miR-486-5p | hsa-miR-486-5p | miR-486-5p | hsa-miR-486-5p |
| 6 | | hsa-miR-18b-5p | hsa-miR-18b-5p | | hsa-miR-18b-5p | hsa-miR-18b-5p |
| 7 | | hsa-miR-21-5p | hsa-miR-21-5p | | hsa-miR-21-5p | hsa-miR-21-5p |
| 8 | | | hsa-miR-126-3p | | hsa-miR-126-3p | hsa-miR-126-3p |
| 9 | | | hsa-miR-20b-5p | | hsa-miR-20b-5p | hsa-miR-20b-5p |
| 10 | | | hsa-miR-100-5p | | hsa-miR-100-5p | hsa-miR-100-5p |
| 11 | | | hsa-miR-10b-5p | | hsa-miR-10b-5p | hsa-miR-10b-5p |
| 12 | hsa-miR-326-5p | hsa-miR-326-5p | hsa-miR-326-5p | | hsa-miR-19a-3p | hsa-miR-19a-3p |

TABLE 14-continued

| miRNA Sequence for Classifiers | | | | | | |
|---|---|---|---|---|---|---|
| | Greedy Pairs Approach | | | Standard BRB-Array Tools Approach | | |
| | 6 | 10 | 20 | 5 | 13 | 24 |
| 13 | | hsa-miR-34a-5p | hsa-miR-34a-5p | | | hsa-miR-34a-5p |
| 14 | | hsa-miR-365a-3p | hsa-miR-365a-3p | | | hsa-miR-199a-5p |
| 15 | | | hsa-miR-190a | | hsa-miR-190a | hsa-miR-190a |
| 16 | | | hsa-miR-31-5p | | | hsa-miR-31-5p |
| 17 | | | hsa-miR-597-5p | | | hsa-miR-18a-5p |
| 18 | | | hsa-miR-301b | | | hsa-miR-194-5p |
| 19 | | | hsa-miR-214-3p | | | hsa-miR-210 |
| 20 | | | hsa-miR-378a-3p | | | hsa-miR-885-5p |
| 21 | | | | | | hsa-miR-324-3p |
| 22 | | | | | | hsa-miR-296-5p |
| 23 | | | | | | hsa-miR-340-5p |
| 24 | | | | | | hsa-miR-30b-3p |

A further statistical study was made using a somewhat different set of control specimens. This study used data from control samples taken from benign lesions, in one case by itself and in the other case combined with data from the control specimens used above, in which specimens were taken from normal mucosal tissue. The results are reported in Tables 15 and 16. For Table 15 four significance levels (0.01, 0.005, 0.001 and 0.0005) were used to decide on the one which gave the lowest cross-validation mis-classification rate, which was 0.01. The same approach was used for Table 16, but in this summary table different significance levels gave optimum results for different statistical tools. The best diagonal linear discriminant analysis classifier consisted of genes significantly different between the classes at the 0.01 significance level. The best 1-nearest neighbor classifier consisted of genes significantly different between the classes at the 0.005 significance level. The best 3-nearest neighbors classifier consisted of genes significantly different between the classes at the 0.005 significance level. The best nearest centroid classifier consisted of genes significantly different between the classes at the 0.01 significance level. The best support vector machines classifier consisted of genes significantly different between the classes at the 0.005 significance level. The best Bayesian compound covariate classifier consisted of genes significantly different between the classes at the 0.005 significance level.

TABLE 15

| Benign Lesion v OSCC | | | | | | | | | |
|---|---|---|---|---|---|---|---|---|---|
| | Sample ID | Class Label | Compound Covariate Predictor Correct | DLDA Correct | 1-Nearest Neighbor Correct | 3-Nearest Neighbor Correct | Nearest Centroid Correct | Support Vector Machine | BAYESIAN Compound Covariate Predictor Correct |
| 1 | 537 | 1 | YES | YES | YES | YES | YES | YES | NA |
| 2 | 117 | 1 | YES | YES | YES | YES | YES | YES | YES |
| 3 | 129421 | 1 | NA | YES | NO | NA | NA | NA | NA |
| 4 | 149 | 1 | YES | YES | YES | YES | YES | YES | YES |
| 5 | 319 | 1 | NO | NO | NO | NO | NO | NO | NO |
| 6 | 367 | 1 | NO | NO | NO | NO | NO | NO | NA |
| 7 | 474 | 1 | YES | YES | YES | YES | YES | YES | YES |
| 8 | 482 | 1 | NO | NO | NO | NO | NO | NO | NO |
| 9 | 490 | 1 | YES | YES | YES | YES | YES | YES | YES |
| 10 | 495 | 1 | YES | YES | NA | YES | YES | YES | NA |
| 11 | 231 | 1 | YES | YES | YES | YES | YES | YES | YES |
| 12 | 305K | 2 | YES | YES | YES | YES | YES | YES | NA |
| 13 | 308 | 2 | NO | NO | NO | NO | NO | NO | NO |
| 14 | 355 | 2 | YES | YES | YES | YES | YES | YES | YES |
| 15 | 357 | 2 | YES | NO | YES | YES | YES | YES | NA |
| 16 | 413 | 2 | YES | YES | YES | YES | YES | YES | YES |
| 17 | 453 | 2 | YES | YES | YES | YES | YES | YES | YES |
| 18 | 463 | 2 | YES | NO | YES | YES | YES | YES | YES |
| 19 | 42810 | 2 | YES | NO | YES | YES | YES | YES | YES |
| 20 | 42310 | 2 | YES | NA | YES | YES | YES | YES | YES |
| 21 | 42910 | 2 | NO | NO | NO | NO | NO | YES | NA |
| 22 | 52710 | 2 | NO | NO | NO | YES | NO | YES | NO |
| 23 | 110 | 2 | YES | NO | YES | YES | YES | YES | NA |
| 24 | 129 | 2 | NO | YES | NA | YES | NO | YES | NO |
| 25 | 329 | 2 | NO | NO | NO | NO | NO | NO | NO |
| 26 | 359 | 2 | NO | NO | NO | NO | NO | NO | NA |
| 27 | 383 | 2 | YES | YES | YES | YES | YES | YES | YES |
| 28 | 449 | 2 | YES | YES | YES | YES | YES | YES | YES |

TABLE 15-continued

Benign Lesion v OSCC

| | Sample ID | Class Label | Compound Covariate Predictor Correct | DLDA Correct | 1-Nearest Neighbor Correct | 3-Nearest Neighbor Correct | Nearest Centroid Correct | Support Vector Machine | BAYESIAN Compound Covariate Predictor Correct |
|---|---|---|---|---|---|---|---|---|---|
| 29 | 466 | 2 | YES | NO | YES | YES | YES | YES | NA |
| 30 | 485 | 2 | NO | NO | YES | NO | NO | NO | NO |
| % Correctly Classified | | | 66 | 52 | 68 | 72 | 66 | 76 | 63 |

Note:
NA denotes the sample is unclassified. These samples are excluded in the computation of the mean percent of correct classification.

TABLE 16

Benign + Normal v. OSCC

| | Sample ID | Class Label | Compound Covariate Predictor Correct | DLDA Correct | 1-Nearest Neighbor Correct | 3-Nearest Neighbor Correct | Nearest Centroid Correct | Support Vector Machine | BAYESIAN Compound Covariate Predictor Correct |
|---|---|---|---|---|---|---|---|---|---|
| 1 | 1920.1 | 1 | NO | NO | NO | NO | NO | NO | NO |
| 2 | 426 | 1 | YES | YES | YES | YES | YES | YES | YES |
| 3 | 514 | 1 | YES | YES | YES | YES | YES | YES | YES |
| 4 | 515 | 1 | YES | YES | YES | YES | YES | YES | YES |
| 5 | 517518 | 1 | NO | NO | NO | NO | NO | NO | NO |
| 6 | 548 | 1 | YES | YES | YES | YES | YES | YES | YES |
| 7 | 117 | 1 | NO | NO | YES | YES | YES | YES | NA |
| 8 | 129421 | 1 | YES | YES | YES | YES | YES | YES | NA |
| 9 | 149 | 1 | YES | YES | YES | YES | NO | YES | NA |
| 10 | 319 | 1 | NO | NO | NO | NO | NO | NO | NO |
| 11 | 367 | 1 | NO | NO | NO | YES | NO | NO | NO |
| 12 | 474 | 1 | YES | NO | YES | YES | YES | YES | NA |
| 13 | 482 | 1 | NO | NO | NO | NO | NO | NO | NO |
| 14 | 490 | 1 | NO | NO | NO | NO | NO | YES | NO |
| 15 | 495 | 1 | YES | YES | YES | YES | YES | YES | YES |
| 16 | 109.1 | 1 | YES | YES | NO | YES | YES | YES | YES |
| 17 | 104.1 | 1 | YES | YES | YES | YES | YES | YES | YES |
| 18 | 115.1 | 1 | YES | YES | YES | YES | YES | YES | YES |
| 19 | 117.1 | 1 | YES | YES | YES | YES | YES | YES | YES |
| 20 | 111.1 | 1 | YES | YES | YES | YES | YES | YES | YES |
| 21 | 100.1 | 1 | YES | YES | YES | YES | YES | YES | YES |
| 22 | 114.1 | 1 | YES | YES | YES | YES | YES | YES | YES |
| 23 | 101.1 | 2 | YES | NO | NO | YES | YES | YES | NA |
| 24 | 231 | 2 | YES | YES | YES | YES | YES | YES | YES |
| 25 | 305K | 2 | NO | NO | NO | NO | NO | NO | NO |
| 26 | 308 | 2 | NO | NO | NO | NO | NO | NO | NO |
| 27 | 355 | 2 | YES | YES | YES | YES | YES | YES | YES |
| 28 | 357 | 2 | YES | YES | YES | YES | YES | YES | YES |
| 29 | 413 | 2 | NO | YES | YES | YES | YES | YES | NA |
| 30 | 453 | 2 | YES | YES | YES | YES | YES | YES | YES |
| 31 | 463 | 2 | YES | NO | YES | YES | YES | YES | NA |
| 32 | 42810 | 2 | NO | NO | YES | YES | YES | NO | NA |
| 33 | 42310 | 2 | YES | NO | YES | YES | YES | YES | NA |
| 34 | 42910 | 2 | NO | YES | NO | NO | NO | YES | NA |
| 35 | 52710 | 2 | NO | YES | NO | NO | NO | NO | NO |
| 36 | 1019.2 | 2 | NO | NO | NO | NO | NO | NO | NO |
| 37 | 1098 | 2 | YES | YES | YES | YES | YES | YES | YES |
| 38 | 28.2 | 2 | NO | NO | NO | NO | NO | YES | NA |
| 39 | 110 | 2 | YES | YES | NO | YES | YES | YES | NA |
| 40 | 129 | 2 | YES | YES | YES | YES | NO | YES | YES |
| 41 | 329 | 2 | NO | NO | NO | YES | NO | NO | NO |
| 42 | 359 | 2 | YES | YES | NO | NO | YES | YES | NA |
| 43 | 383 | 2 | YES | YES | YES | YES | YES | YES | YES |
| 44 | 449 | 2 | YES | YES | YES | YES | YES | YES | YES |
| 45 | 466 | 2 | YES | YES | YES | YES | YES | YES | YES |
| 46 | 485 | 2 | YES | YES | YES | NO | NO | YES | NA |
| % Correct Classification | | | 65 | 63 | 63 | 72 | 65 | 76 | 66 |

Note:
NA denotes the sample is unclassified. These samples are excluded in the computation of the mean percent of correct classification.

In this statistical study the first approach utilized four miRNA sequences in creating classifiers while the latter approaches utilized 18 sequences. They are listed in rank order with their t-values in Table 17.

TABLE 17

| | Benign Lesion Controls Alone | | Benign Lesion and Normal Control | |
|---|---|---|---|---|
| | Sequence | t-value | Sequence | t-value |
| 1 | hsa-miR-873-5p | −3.642 | hsa-mir-7-5p | −4.191 |
| 2 | hsa-miR-196a-5p | −3.038 | hsa-miR-101-3p | −3.909 |
| 3 | hsa-miR-765 | −3.093 | hsa-miR-873-5p | −3.936 |
| 4 | hsa-miR-26a-5p | 2.878 | hsa-miR-301a-3p | −3.511 |
| 5 | | | hsa-miR-23a-3p | 3.459 |
| 6 | | | hsa-miR-574-3p | 3.429 |
| 7 | | | hsa-miR-19b-3p | −3.405 |
| 8 | | | hsa-miR-196a-5p | −3.420 |
| 9 | | | hsa-miR-296-5p | 3.266 |
| 10 | | | hsa-miR-20b-5p | −3.168 |
| 11 | | | hsa-miR-142-3p | −2.969 |
| 12 | | | hsa-miR-365a-3p | 2.943 |
| 13 | | | hsa-miR-190a | −2.964 |
| 14 | | | hsa-miR-186-5p | −2.930 |
| 15 | | | hsa-miR-486-5p | 2.800 |
| 16 | | | hsa-miR-34a-5p | 2.742 |
| 17 | | | hsa-miR-424-5p | −2.714 |
| 18 | | | hsa-miR-19a-3p | −2.693 |

WORKING EXAMPLE

Sample Acquisition

Brush biopsy samples were collected from patients in the Oral and Maxillofacial Surgery Clinic in the University of Illinois Medical Center just prior to diagnostic biopsy or extirpative surgery. The clinical characterization of the samples are provided in Table 18. Details on some of the OSCC samples are provided in Table 19. Control samples were from subjects who on clinical examination revealed no suspicious lesions, the majority but not all were followed up over a year. The protocol used to obtain samples from patients after informed consent was approved by the Office for the Protection of Research Subjects of the University of Illinois at Chicago, the local Institutional Review Board.

TABLE 18

Sample Characterization

| | Method of RNA analysis | | | |
|---|---|---|---|---|
| | miRNAseq | | RT-PCR | |
| Status | OSCC | Normal | OSCC | Normal |
| Total Number of Subjects | 20 | 7 | 20 | 17 |
| Age | 37-90, 61.5 | 26-71, 56 | 37-90, 62 | 26-76, 52 |
| Gender | 12M/8F | 3M/4F | 12M/8F | 11M/7F |
| Site[a] | 10 T, 7 LG, 2 FOM, 1BU | 4T, 3LM | 10T, 8LG, 1Bu, 1FOM | 13T, 3LG, 1 Bu |
| History of Tobacco/Betel Nut | 9 | 0 | 8 | 8 |

[a]Tongue, T; Lower Gingiva, LG; Floor of Mouth, FOM; Buccal, Bu

TABLE 19

Selected Subject Characterization

| | Site | Gender | Age | History of Exposure | Classification | Grade |
|---|---|---|---|---|---|---|
| OSCC383 | T | M | 45 | Betel | T4AlphaN0M0 | II |
| OSCC 578 | T | F | 57 | Tobacco | T1N0M0 | I |
| OSCC583 | T | M | 56 | Tobacco | T1N0M0 | I |
| OSCC589 | FOM | M | 69 | Tobacco | T1N0M0 | II |

a. Tongue, T; Floor of Mouth, FOM

Histopathological Confirmation

A total 23 subjects with OSCC all were diagnosed by surgical biopsy followed by histopathology and then this was confirmed post surgery (While the OSCC sample sets for both types of RNA analysis largely overlapped they were not completely coincident thus giving a total of 23 samples). For 17 of the samples, the slides were available and these were reviewed by a third pathologist who confirmed the diagnosis as OSCC, this included the three cases that had equivocal miRNA-based identification, OSCC305K, OSCC355 and OSCC413. OSCC329, 357, 42910, 383, 583 and 589 were only doubly confirmed.

RNA Purification

RNeasy chromatography (Qiagen, Germantown, Md., USA) was used to remove mRNA followed by ethanol addition and RNeasy MinElute chromatography (Qiagen) to bind then elute small RNAs, including mature miRNA as described in "Similar Squamous Cell Carcinoma Epithelium microRNA Expression in Never Smokers and Ever Smokers" by Kolokythas A, Zhou Y, Schwartz J L, Adami G R. in PloS one. 2015; 10(11):e0141695.

miRNA Quantification by miRNAseq

Small RNA libraries were constructed from 100 ng small RNA and sequenced at the W. M. Keck Center for Comparative and Functional Genomics at the University of Illinois at Urbana-Champaign under the direction of Hector Alvaro. Small RNA libraries were constructed from the RNA samples using the TruSeq Small RNA Sample Preparation Kit (Illumina, San Diego, Calif., USA) with the modifications described in "Plasma Exosomal miRNAs in Persons with and without Alzheimer Disease: Altered Expression and Prospects for Biomarkers" by Lugli G, Cohen A M, Bennett D A, Shah R C, Fields C J, Hernandez A G, et al. in PloS one. 2015; 10(10):e0139233. Epub 2015 Oct. 2, with size selection of pooled barcoded libraries post-PCR amplification so to enrich for small RNAs 18 to 50 nt in length. The final libraries were quantified by Qubit (Life Technologies, Carlsbad, Calif., USA) and the average size was determined on an Agilent Bioanalyzer High Sensitivity DNA chip (Agilent Technologies, Santa Clara, Calif., USA). The libraries were sequenced from one end of the molecule to a total read length of 50 nt on the Illumina HiSeq2500. The raw.bcl files were converted into demultiplexed FASTQ files with Casava 1.8.2 (Illumina).

miRNAseq Data Analysis

Sequence files were received as FASTQ files, which were imported into Galaxy where adaptors were trimmed and quality assessed. Sequences of 17 bases and more were preserved and the collapse program in Galaxy was used to combine and count like sequences. FASTA files were uploaded in sRNAbench 1.0 which is now part of RNAtools http://bioinfo5.ugr.es/srnatoolbox/srnabench/ as described in "miRanalyzer: an update on the detection and analysis of microRNAs in high-throughput sequencing experiments" by Hackenberg M, Rodriguez-Ezpeleta N, Aransay A M. in Nucleic Acids Res. 2011; 39(Web Server issue):W132-8 and "sRNAtoolbox: an integrated collection of small RNA research tools" by Rueda A, Barturen G, Lebron R, Gomez-Martin C, Alganza A, Oliver J L, et al. in Nucleic Acids Res. 2015; 43(W1):W467-73. We used the h19 genome build miRNA library and selected 17 as seed length for alignment. The output Excel files of read counts for each known miRNA for each sample were combined into one and post-normalization was imported into BRB-Array Tools to allow class comparison of differentially expressed miRNAs excluding miRNAs undetectable in less than 40% of samples as described in "A prototype tobacco-associated oral squamous cell carcinoma classifier using RNA from brush cytology" by Kolokythas A, Bosman M J, Pytynia K B, Panda S, Sroussi H Y, Dai Y, et al. in the Journal of oral pathology & medicine: official publication of the International Association of Oral Pathologists and the American Academy of Oral Pathology. 2013; 42(9):663-9. Epub 2013 Apr. 18 and "Analysis of gene expression data using BRB-ArrayTools" by Simon R, Lam A, Li M C, Ngan M, Menenzes S, Zhao Y. Cancer informatics. 2007; 3:11-7. Epub 2007 Jan. 1. This program was used to generate heat maps that allow a visualization of coordinately differentially expressed miRNAs. Tumor samples are more frequently contaminated with blood, which provide an excess of RBC markers, miR-451a, miR-144-3p and miR-144-5p, which for the purpose of this study are ignored. The class prediction tools of the site were used to test the 7 different class prediction algorithms and their ability to generate using leave-one-out cross-validation, a classifier to differentiate the two samples types and then test the composite classifier on the individual samples using leave-one-out cross-validation. Optimization of the cut-off for significance levels for differences in miRNA quantities between classes was embedded in classifier generation so to avoid bias. While miRNAseq has the advantage that raw data can be re-evaluated as more miRNAs are identified in the future, the RT-qPCR approach was more sensitive even without an amplification step.

miRNA Quantification by qRT-PCR Arrays

Most tumor samples were analyzed by RT-qPCR as described in "Similar Squamous Cell Carcinoma Epithelium microRNA Expression in Never Smokers and Ever Smokers" by Kolokythas A, Zhou Y, Schwartz J L, Adami G R. in PloS one. 2015; 10(11):e0141695. Ten nanograms RNA from the additional tumor samples described in Table 16 and most normal samples was reverse transcribed in 5 ul reactions using the miRCURY LNA Universal RT microRNA PCR, Polyadenylation and cDNA synthesis kit (Exiqon, Woburn, Mass., USA). cDNA was diluted 20-fold and assayed in 10 ul PCR reactions according to the protocol for miRCURY LNA Universal RT microRNA PCR against a panel of 4 miRNAs and a spike-in control for cDNA synthesis. When duplicate samples were available from a single lesion, the higher yield sample was subjected to a scaled-up cDNA synthesis and was assayed by RT-qPCR on the microRNA Ready-to-Use PCR, Human panel I (Exiqon), which includes 372 miRNA primer sets. The amplification was performed in an Applied Biosystems Viia 7 RT-qPCR System (Life Technologies) in 384-well plates. The amplification curves were analyzed for Ct values using the built-in software, with a single baseline and threshold set manually for each plate.

Analysis of RT-qPCR array miRNA generated data was done as described for miRNAseq except the data was already log transformed prior to analysis with the BRB-Array Tools program. Rank product analysis was done to confirm some likely differentially expressed miRNAs as described in "Rank products: a simple, yet powerful, new method to detect differentially regulated genes in replicated microarray experiments" by Breitling R, Armengaud P, Amtmann A, Herzyk P. in FEBS letters. 2004; 573(1-3):83-92. Epub 2004 Aug. 26 and RankProdlt: A web-interactive Rank Products analysis tool. by Laing E, Smith C P. in BMC research notes. 2010; 3:221. Epub 2010 Aug. 10

Expression Data Normalization

For RT-PCR generated expression levels, Excel was used to normalize expression to a reference sample based on comparison to the value of 40 miRNAs in the panel that were found to be present in every sample. For miRNAseq the same methodology was used to normalize expression among the expression values except an overlapping but different set of consistently detected 50 miRNAs was used to determine the normalization factor.

The samples used to identify a patient likely to have OSCC can be taken from body fluids or from mucosal epithelium. For general screening plasma, serum or saliva are convenient sources. As a sample source, saliva has the advantage of being directly sourced from the oral cavity. The saliva sample may conveniently be whole saliva, extracted cells or supernatant. For discriminating between benign oral lesions and OSCCC lesions a sample obtained by brush cytology is convenient.

It is convenient to use a statistically derived classifier that has a prediction accuracy of at least 80% in distinguishing between OSCC tissue and benign tissue when either the tissue, as in the case of an oral lesion, is sampled directly by brush cytology or when the sample is a bodily fluid such as saliva.

In identifying patients likely to have OSCC it is helpful to examine the relative prevalence of miRNA sequences hsa-miR-130-3p, hsa-miR-7-5p, hsa-miR-101-3p and hsa-miR-146b-5p. In one embodiment, sequence miR-365a-3p and hsa-miR-21-5p are also examined, while in another embodiment sequences hsa-miRNA-486-5p, hsa-miR-18b-5p, hsa-miRNA-126-3p, hsa-miR-20b-5p, hsa-miR-100-5p, hsa-miR-19a-3p, hsa-miR-190a and hsa-miRNA-10b-5 are also examined. In the particular case of distinguishing between benign oral lesions and OSCC it is helpful to examine the relevant prevalence of sequences hsa-miR-196a-5p and hsa-miR-873-5p. In selecting particular sequences to examine for the development of a tool for identification it is convenient to use those in which relative level of expression or prevalence in the normal cells is at least about double or one half of that in the OSCC cells.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A process comprising;

a. obtaining a sample taken by brush cytology containing miRNA from essentially epithelial cells from a patient's oral cavity;

b. selecting a plurality of miRNA sequences from a set of miRNA sequences dawn from the human transcriptome that have previously been determined to have levels of expression of one half or less and/or double or more in human epithelial cells afflicted with OSCC compared to those of cells not so afflicted by obtaining samples by brush cytology from two populations of human subjects, one afflicted with OSCC and one not so afflicted; and c. measuring the levels of expression of the selected plurality of miRNA sequences.

2. The process of claim 1 wherein the levels of expression of a panel of miRNA sequences including at least all of hsa-miR-130-3p, hsa-miR-7-5p, hsa-miR-101-3p and hsa-miR-146b-5p are determined.

3. The process of claim 2 wherein the levels of expression of the miRNA sequences hsa-miR-365a-3p and hsa-miR-21-5p are also determined.

4. The process of claim 3 wherein the levels of expression of the miRNA sequences hsa-miRNA-486-5p, hsa-miR-18b-5p, hsa-miRNA-126-3p, hsa-miR-20b-5p, hsa-miR-100-5p, hsa-miR-19a-3p, hsa-miR-190a and hsa-miRNA-10b-5 are also determined.

5. The process of claim 1 wherein the levels of expression of a panel of miRNA sequences including at least all of hsa-miR-101-3p, has-miR-186-5p, hsa-miR-18a-5p and hsa-miR-423-5p or all of hsa-miR-101-3p, hsa-miR-142-3p and hsa-miR-146b-5p or all of hsa-miR-186-5p, hsa-miR-146b-5p, hsa-miR-101-3p and hsa-miR-142-3p or all of hsa-miR-873-5p are determined.

6. A process to discriminate between benign oral lesions and OSCC comprising;

a. obtaining a sample taken by brush cytology of essentially the epithelial cells of the lesion;

b. selecting a plurality of miRNA sequences from a set of miRNA sequences dawn from the human transcriptome that have previously been determined to have levels of expression of one half or less and/or double or more in human epithelial cells afflicted with OSCC compared to those of cells not so afflicted by obtaining samples by brush cytology from two populations of human subjects, one afflicted with OSCC and one not so afflicted; and c. measuring the levels of expression of the selected plurality of miRNA sequences.

7. The process of claim 6 wherein the levels of expression of a panel including both of the miRNA sequences hsa-miR-196a-5p and hsa-miR-873-5p are determined.

8. The process of claim 6 wherein the levels of expression of the sample are examined by a classifier developed by applying a statistical tool to the expression levels of a panel of miRNA sequences of samples of normal and OSCC cells.

9. The process of claim 1 wherein the selected plurality comprises at least six miRNA sequences.

10. The process of claim 6 wherein the selected plurality comprises at least six miRNA sequences.

11. The process of claim 1 wherein the set of miRNA sequences is within the 372 miRNA sequences covered by the Exiqon Human panel 1.

12. The process of claim 1 wherein the set of miRNA sequences is drawn from hsa-miRNA sequences 210, 375, 100-5p, 101-3p, 10a-5p, 10b-5p, 126-3p, 126-5p, 127-3p, 130b-3p, 135a-5p, 135b-5p, 142-3p, 146a-5p, 146b-5p, 150-5p, 155-5p, 185-3p, 187-3p, 18a-5p, 18b-5p, 190a-5p, 194-5p, 196a-5p, 199a-5p, 20b-5p, 21-5p, 214-3p, 218-5p, 296-5p, 301a-3p, 30b-3p, 31-3p, 31-5p, 328-3p, 339-5p, 340-5p, 345-5p, 34a-5p, 3605-3p, 363-3p, 423-5p, 424-5p, 454-3p, 486-5p, 597-5p, 671-5p, 7-5p, 766-3p, 7d-3p, 873-5p, 885-5p, and 99b-3p.

13. A process comprising;

a. obtaining a sample from saliva containing miRNA from essentially epithelial cells from a patient's oral cavity:

b. selecting hsa-miRNA sequences 130-3p, 7-5p, 101-3p and 146b-5p; and c. measuring the level of expression of the selected miRNA sequences.

14. The process of claim 6 wherein the level of expression of the miRNA sequences is subjected to a statistically derived classifier which has a prediction accuracy of at least 80% in distinguishing between OSCC tissue and benign tissue.

15. The process of claim 6 wherein the set of miRNA sequences is drawn from hsa-miRNA sequences 210, 375, 100-5p, 101-3p, 10a-5p, 10b-5p, 126-3p, 126-5p, 127-3p, 130b-3p, 135a-5p, 135b-5p, 142-3p, 146a-5p, 146b-5p, 150-5p, 155-5p, 185-3p, 187-3p, 18a-5p, 18b-5p, 190a-5p, 194-5p, 196a-5p, 199a-5p, 20b-5p, 21-5p, 214-3p, 218-5p, 296-5p, 301a-3p, 30b-3p, 31-3p, 31-5p, 328-3p, 339-5p, 340-5p, 345-5p, 34a-5p, 3605-3p, 363-3p, 423-5p, 424-5p, 454-3p, 486-5p, 597-5p, 671-5p, 7-5p, 766-3p, 7d-3p, 873-5p, 885-5p, and 99b-3p.

16. The process of claim 1 wherein the results of the measurement are subjected to a statistically derived classifier which has a prediction accuracy of at least 80% in distinguishing between OSCC tissue and benign tissue.

17. The process of claim 8 wherein the statistical tool is selected from the group consisting of compound covariate predictor, diagonal linear discriminant analysis, 1-nearest neighbor, 3-nearest neighbors, nearest centroid, support vector machines and bayesian compound covariate predictor.

18. The process of claim 8 wherein the probability that the discrimination is correct is at least about 80%.

19. The process of claim 13 wherein the epithelial cell miRNA is obtained from saliva supernatant.

20. The process of claim 13 wherein the epithelial cell miRNA is obtained from cells isolated from saliva.

* * * * *

UNITED STATES PATENT AND TRADEMARK OFFICE

CERTIFICATE OF CORRECTION

PATENT NO. : 11,639,528 B2
APPLICATION NO. : 15/774005
DATED : May 2, 2023
INVENTOR(S) : Guy Adami et al.

It is certified that error appears in the above-identified patent and that said Letters Patent is hereby corrected as shown below:

In the Specification

The following should appear in Column 1 immediately after the title:
STATEMENT REGARDING FEDERALLY SPONSORED RESEARCH
This invention was made with government support under grant number 1346486, awarded by the National Science Foundation. The Government has certain rights in this invention.

Signed and Sealed this
Sixth Day of June, 2023

Katherine Kelly Vidal

Katherine Kelly Vidal
*Director of the United States Patent and Trademark Office*